(12) United States Patent
Mays et al.

(10) Patent No.: US 9,708,434 B2
(45) Date of Patent: Jul. 18, 2017

(54) MULTIGRAFT COPOLYMERS AS SUPERELASTOMERS

(75) Inventors: Jimmy W. Mays, Knoxville, TN (US); Samuel P. Gido, Hadley, MA (US); Roland Weidisch, Halle (DE); Liane Weidisch, legal representative, Halle (DE); Christina Weidisch, legal representative, Halle (DE)

(73) Assignees: University of Tennessee Research Foundation, Knoxville, TN (US); University of Massachusetts, Boston, MA (US); Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 13/877,229

(22) PCT Filed: Sep. 30, 2011

(86) PCT No.: PCT/US2011/054345
§ 371 (c)(1),
(2), (4) Date: Dec. 23, 2013

(87) PCT Pub. No.: WO2012/045006
PCT Pub. Date: Apr. 5, 2012

(65) Prior Publication Data
US 2014/0161858 A1 Jun. 12, 2014

Related U.S. Application Data

(60) Provisional application No. 61/389,025, filed on Oct. 1, 2010.

(51) Int. Cl.
| | | |
|---|---|---|
| *C08F 299/00* | (2006.01) | |
| *C09J 151/00* | (2006.01) | |
| *A61L 31/10* | (2006.01) | |
| *C09D 151/00* | (2006.01) | |
| *C08L 51/00* | (2006.01) | |
| *A61L 31/16* | (2006.01) | |
| *C08F 279/02* | (2006.01) | |
| *C08K 3/00* | (2006.01) | |
| *C09D 151/04* | (2006.01) | |
| *C09J 151/04* | (2006.01) | |
| *A61L 29/04* | (2006.01) | |
| *A61L 31/04* | (2006.01) | |

(52) U.S. Cl.
CPC ............ *C08F 299/00* (2013.01); *A61L 29/04* (2013.01); *A61L 31/04* (2013.01); *A61L 31/10* (2013.01); *A61L 31/16* (2013.01); *C08F 279/02* (2013.01); *C08K 3/0033* (2013.01); *C08L 51/003* (2013.01); *C09D 151/003* (2013.01); *C09D 151/04* (2013.01); *C09J 151/003* (2013.01); *C09J 151/04* (2013.01); *Y10T 428/2918* (2015.01); *Y10T 428/31645* (2015.04); *Y10T 428/31667* (2015.04); *Y10T 428/31692* (2015.04); *Y10T 428/31899* (2015.04); *Y10T 428/31938* (2015.04); *Y10T 442/20* (2015.04)

(58) Field of Classification Search
None
See application file for complete search history.

(56) References Cited

U.S. PATENT DOCUMENTS

| | | | |
|---|---|---|---|
| 4,335,723 A | 6/1982 | Patel | |
| 4,481,323 A | 11/1984 | Sterling | |
| 4,886,062 A | 12/1989 | Wiktor | |
| 5,079,090 A * | 1/1992 | Joseph et al. | ................. 428/343 |
| 5,210,147 A * | 5/1993 | Southwick | ........... C09J 153/025 525/314 |
| 5,741,857 A | 4/1998 | Esneault et al. | |
| 5,837,008 A | 11/1998 | Berg | |
| 5,843,172 A | 12/1998 | Yan | |
| 5,851,217 A | 12/1998 | Wolff et al. | |
| 5,873,904 A | 2/1999 | Ragheb et al. | |
| 6,344,035 B1 | 2/2002 | Chudzik et al. | |
| 6,368,658 B1 * | 4/2002 | Schwarz et al. | ............. 427/2.15 |
| 7,049,373 B2 | 5/2006 | Matyjaszewski et al. | |
| 7,163,555 B2 | 1/2007 | Dinh | |
| 7,435,255 B1 | 10/2008 | Rao | |
| 7,619,036 B2 | 11/2009 | Mays et al. | |

(Continued)

FOREIGN PATENT DOCUMENTS

| | | |
|---|---|---|
| EP | 0235482 | 9/1987 |
| EP | 2218753 A1 | 8/2010 |

(Continued)

OTHER PUBLICATIONS

Uhrig et al. (Macromolecules 2002, 35, 7182-7190).*

(Continued)

*Primary Examiner* — Patricia Duffy
*Assistant Examiner* — Garen Gotfredson
(74) *Attorney, Agent, or Firm* — Jenkins, Wilson, Taylor & Hunt, P.A.

(57) ABSTRACT

Thermoplastic elastomer compositions are described comprising multigraft copolymers. The multigraft copolymers can comprise a rubbery polymeric backbone and a plurality of glassy polymeric side chains, each attached at one of a plurality of branch points randomly spaced along the backbone. The copolymer materials have high tensile strength, high strain at break, and low residual strain after elongation. The compositions can be used as adhesives and in a wide variety of high tech, medical, and commodity applications.

29 Claims, 22 Drawing Sheets

(56) References Cited

U.S. PATENT DOCUMENTS

| | | | |
|---|---|---|---|
| 7,794,491 | B2 | 9/2010 | Von Oepen |
| 8,061,533 | B2 | 11/2011 | Mays et al. |
| 2002/0103295 | A1 | 8/2002 | Eichenauer |
| 2003/0180488 | A1 | 9/2003 | Lim et al. |
| 2005/0245645 | A1 | 11/2005 | Howie, Jr. |
| 2008/0193818 | A1 | 8/2008 | Mays |
| 2008/0194716 | A1 | 8/2008 | Sasagawa et al. |
| 2009/0028356 | A1 | 1/2009 | Ambrose et al. |
| 2009/0285974 | A1 | 11/2009 | Kerrigan et al. |
| 2010/0190671 | A1 | 7/2010 | Stoehr et al. |
| 2010/0210745 | A1 | 8/2010 | McDaniel et al. |

FOREIGN PATENT DOCUMENTS

| | | |
|---|---|---|
| GB | 2008140 A | 5/1979 |
| RU | 2483083 | 5/2013 |
| SU | 712027 | 1/1980 |
| WO | WO 2012/045006 | 4/2012 |
| WO | WO 2015/196093 | 12/2015 |

OTHER PUBLICATIONS

International Search Report and Written Opinion dated Feb. 14, 2012 for International Patent Application No. PCT/US2011/054345, pp. 1-15.

European Extended Search Report dated Jun. 27, 2014 for co-pending European Patent Application No. 11830015.1, pp. 1-3.

Singapore Search Report and Written Opinion dated Jul. 11, 2014 for co-pending Singapore Patent Application No. 201302146-4, pp. 1-18.

Zhu, Y. et al., "Morphology and Tensile Properties of Multigraft Copolymers with Regularly Spaced Tri-, Tetra-, and Hexafunctional Junction Points," Macromolecules, 2006, No. 39, pp. 4428-4436.

Weidisch, R. et al., "Tetrafunctional Multigraft Copolymers as Novel Thermoplastic Elastomers," Macromolecules, 2001, No. 34, pp. 6333-6337.

Mays, et al., "Synthesis and Structure—Property Relationships for Regular Multigraft Copolymers," Macromol. Symp, 2004, No. 215, pp. 111-126.

Uhrig, D. et al., "Synthesis of Combs, Centipedes, and Barbwires: Poly(isoprene-*graft*-styrene) Regular Multigraft Copolymers with Trifunctional, Tetrafunctional and Hexafunctional Branch Points," Macromolecules, 2002, No. 35, pp. 7182-7190.

Schlegel, et al., "Investigations on Mechanical Properties of PI-PS Multigraft Copolymers," European Polymer Journal, 2009, No. 45, pp. 2902-2912.

Alward et al., "Effect of Arm Number and Arm Molecular Weight on the Solid-State Morphology of Poly(styrene-isoprene) Star Block Copolymers," Macromolecules, vol. 19, p. 215 (1986).

Beyer et al., "Graft Copolymers with Regularly Spaced, Tetrafunctional Branch Points: Morphology and Grain Structure," Macromolecules, vol. 33, pp. 2039-2048 (2000).

Beyer et al., "Morphological Behavior of A2B2 Star Block Copolymers," J. Polymer Sci.: Part B, Polymer Physics, 37, 3392 (1999).

Beyer et al., "Morphological Behavior of A5B Miktoarm Star Block Copolymers," Macromolecules, 32, 6604 (1999).

Beyer et al., "Morphology of Vergina Star 16-Arm Block Copolymers and Scaling Behavior of Interfacial Area with Graft Point Functionality," Macromolecules, 30, 2373 (1997).

Burgaz et al., "T-Junction Grain Boundaries in Block Copolymer-Homopolymer Blends," Macromolecules, 33, 8739-8745 (2000).

Chang et al., "Analysis of Grain Structure in Partially Ordered Block Copolymers by Depolarized Light Scattering and Transmission Electron Microscopy," Macromolecules. vol. 35 pp. 4437-4447 (2002).

Communication pursuant to Rule 71(3) EPC corresponding to co-pending European Patent Application No. 11 830 015.1, mailed Jun. 23, 2015.

Decision to Grant a European Patent pursuant to Article 97(1) EPC corresponding to European Patent Application No. 11830015.1, mailed on Nov. 19, 2015.

Examination Report corresponding to co-pending Singapore Patent Application No. 2013021464 mailed Feb. 27, 2015.

Falk et al., "New Thermoplastic Elastomers, Styrene Grafts on Lithiated Polydienes and Their Hydrogenated Counterparts," Rubber Chem. Technol. vol. 46 pp. 1044-1054 (1973).

Gido et al., "Interfacial Curvature in Graft and Diblock Copolymers and Implications for Long-Range Order in Cylindrical Morphologies," Macromolecules, vol. 30, p. 6771 (1997).

Gido et al., "Lamellar Diblock Copolymer Grain Boundary Morphology. 1. Twist Boundary Characterization," Macromolecules, vol. 26, p. 4506 (1993).

Gido et al., "Synthesis, Characterization, and Morphology of Model Graft Copolymers with Trifunctional Branch Points," Macromolecules, vol. 29, pp. 7022-7028 (1996).

Hadjichristidis et al., "Anionic Polymerization: High Vacuum Techniques," J. Polym. Sci., Polym. Chem. Ed., vol. 38, pp. 3211-3234 (2000).

Hadjichristidis et al., "Conformation of Poly(isoprene-g-Styrene) in Dilute Solution," Journal of Polymer Science: Polymer Physics Edition. vol. 16, p. 851-858 (1978).

Hong et al., "1,3-Cyclohexadiene Polymers. II. Near-Monodisperse Star and Star-Block Polymers Based on Poly(1,3-cyclohexadiene)," Macromolecules, vol. 34, p. 2482-2487 (2001).

Hong, K. et al., "1,3-Cyclohexadiene Polymers. I. Anionic Polymerization," Macromolecules, vol. 34, p. 782-786 (2001).

Hong, K. et al., "1,3-Cyclohexadiene Polymers. III. Synthesis and Characterization of Poly(1,3-cyclohexadiene-block-styrene," Macromolecules, vol. 34, p. 3540-3547 (2001).

Iatrou et al., "Regular Comb Polystyrenes and Graft Polyisoprene/Polystyrene Copolymers with Double Branches ("Centipedes"). Quality of (1,3-Phenylene)bis(3-methyl-1-phenylpentylidene)dilithium Initiator in the Presence of Polar Additives," Macromolecules, vol. 31, pp. 6697-6701 (1998).

Lee et al., "(-Shaped double-graft copolymers: effect of molecular architecture on morphology," Polymer. vol. 39, p. 4631-4638 (1998).

Lee et al., "Asymmetric Single Graft Block Copolymers: Effect of Molecular Architecture on Morphology," Macromolecules, vol. 30, pp. 3732-3738 (1997).

Lee et al., "H-shaped double graft copolymers: Effect of molecular architecture on morphology," J. Chem. Phys., vol. 107, pp. 6460-6469 (1997).

Milner, S. T., "Chain Architecture and Asymmetry in Copolymer Microphases," Macromolecules, vol. 27, pp. 2333-2335 (1994).

Napandensky et al., "Characterization of Highly Sulfonated SIBS Polymer Partially Neutralized with Mg+2 Cations" Army Research Laboratory. (2008).

Notification Concerning Transmittal of International Preliminary Report on Patentability (Chapter I of the Patent Cooperation Treaty), corresponding to PCT/US2011/054345, mailed on Apr. 11, 2013.

Pochan et al., "Morphologies of Microphase-Separated A2B Simple Graft Copolymers," Macromolecules, vol. 29, p. 5091 (1996).

Pochan et al., "Morphologies of Microphase-Separated Conformationally Asymmetric Diblock Copolymers," J. Polymer Sci.: Part B, Polymer Physics, vol. 35, p. 2629 (1997).

Tate et al., "Metallation of Unsaturated Polymers and Formation of Graft Copolymers," Journal of Polymer Science: Part A-1. vol. 9 pp. 139-145 (1971).

Thomas et al., "Ordered Packing Arrangements of Spherical Micelles of Diblock Copolymers in Two and Three Dimensions," Macromolecules, vol. 20, p. 2934 (1987).

Thomas, B. L., "Ordered Bicontinuous Double-Diamond Structure of Star Block Copolymers: A New Equilibrium Microdomain Morphology," Macromolecules, vol. 19, p. 2197 (1986).

Tsoukatos et al., "Model Linear Block Co-, Ter-, and Quaterpolymers of 1,3-Cyclohexadiene with Styrene, Isoprene, and Butadiene," Macromolecules, vol. 35, pp. 7928-7935 (2002).

(56) References Cited

OTHER PUBLICATIONS

Winey et al., "Ordered morphologies in binary blends of diblock copolymer and homopolymer and characterization of their intermaterial dividing surfaces," J. Chem. Phys., vol. 95, p. 9367 (1991).
Xenidou et al., "Morphology of Model Graft Copolymers with Randomly Placed Trifunctional and Tetrafunctional Branch Points," Macromolecules, vol. 31, p. 7659 (1998).
Driva et al., "Anionic homo- and copolymerization of double-tailed macromonomers: A route to novel macromolecular architectures," Journal of Polymer Science Part A: Polymer Chemistry. vol. 43, No. 18 pp. 4070-4078 (2005) [Abstract].
Nikopoulou et al., "Anionic homo- and copolymerization of styrenic triple-tailed polybutadiene macromonomers," Journal of Polymer Science Part A: Polymer Chemistry. vol. 45, No. 16 pp. 3513-3523 (2007) [Abstract].
Al-Mualhem, and Knauss, "Graft Copolymers from Star-Shaped and Hyperbranched Polystyrene Macromonomers," J. Polym. Scie. Polym. Chem. Ed. vol. 39 pp. 3547-3555 (2001).
Balsara et al., "Anisotrophy of Lamellar Block Copolymer Grains," Physical Review E. vol. 66 Article # 052802 (2002).
Bi and Fetters, "Synthesis and Properties of Block Copolymers. 3. Polystyrene-Polydiene Star Block Copolymers," Macromolecules. vol. 9 pp. 732-742 (1976).
Cameron, and Qureshi, "Grafting of Polybutadiene Functionalised with Chlorosilane Groups," Makromol. Chem., Rapid Commun. vol. 2 pp. 287-291 (1981).
Crawford et al., "Structure/property relationships in polystyrene-polyisobutylene-polystyrene block copolymers," Thermochimia acta. pp. 125-134 (2001).
David et al., "Core-Shell Cylinder Morphology in Poly(styrene-b-1,3-cyclohexadiene) Diblock Copolymers," Macromolecules. vol. 32 p. 3216-3226 (1999).
Duan et al., "Deformation Behavior of Sphere-Forming Trifunctional Multigraft Copolymer," Macromolecules, vol. 41 pp. 4565-4568 (2008).
Duan et al., "Morphology and Deformation Mechanisms and Tensile Properties of Tetrafunctional Multigraft Copolymers," Macromolecules. vol. 42 pp. 4155-4164 (2009).
Hadjichristidis et al., "Morphology and miscibility of miktoarm styrene-diene copolymers and terpolymers," Macromolecules. vol. 26 pp. 5812-5815 (1993).
Iatrou et al., "Hydrodynamic properties of model 3-miktoarm star copolymers," J. Polym. Sci., Polym. Phys. Ed. vol. 33 pp. 1925-1932 (1995).
Knauss et al., "Polystyrene with Dendritic Branching by Convergent Living Anionic Polymerization," Macromolecules. vol. 33 pp. 3557-3568 (2000).
Mamodia et al., "Effect of Microdomain Structure and Process Conditions on the Mechanical Behavior of Cylindrical Block Copolymer Systems," Macromolecules. vol. 40 pp. 7320-7328 (2007).
Mays, "Synthesis of "simple graft" poly(isoprene-g-styrene) by anionic polymerization," Polymer Bulletin. vol. 23 pp. 247-250 (1990).
Mijovic et al., "Effect of Molecular Architecture on Dynamics of Multigraft Copolymers: Combs, Centipedes, and Barbwires," Macromolecules. vol. 36 pp. 7640-7651 (2003).
Minoura and Harada, "Anionic Graft Copolymerization of Diene Polymers with Vinyl Monomers," J. Poly. Sci. Part A-1, vol. 7 pp. 3-14 (1969).
Minoura et al., "Lithiation of Diene Polymers," J. Polym. Sci. Part A-1, vol. 6 pp. 559-573 (1968).
Morton et al., "Preparation and properties of monodisperse branched polystyrene," J. Polym. Sci. vol. 57 pp. 471-482 (1962).
Pantazis et al., "Anionic Polymerization of Styrenic Macromonomers," Macromolecules. vol. 36 pp. 3783-3785 (2003).
Park et al., "Utility of Interaction Chromatography for Probing Structural Purity of Model Branched Block Copolymers," Macromolecules. vol. 36 p. 5834-5838 (2003).
Pochan et al. "Morphological Transitions in an I2S Simple Graft Block Copolymer: From Folded Sheets to Folded Lace to Randomly Oriented Worms at Equilibrium," Macromolecules. vol. 29 pp. 5099-5105 (1996).
Rahman et al., "Synthesis and Dilute Solution Properties of Well-Defined H-Shaped Polybutadienes," Macromolecules. vol. 41 pp. 8225-8230 (2008).
Retsos et al., "Interfacial Tension in Binary Polymer Blends in the Presence of Block Copolymers: Effects of Additive Architecture and Composition," Macromolecules. vol. 37 pp. 524-537 (2004).
Schlegel et al., "Stress softening of mulitgraft copolymers," Polymer. vol. 50 pp. 6297-6304 (2009).
Staudinger et al., "Interpretation of hysteresis behaviour of PI-PS multigraft copolymers of adapting to the dynamic flocculation model," European Polymer Journal. vol. 44 pp. 3790-3796 (2008).
Staudinger et al., "Mechanical Properties and Hysteresis Behaviour of Multigraft Copolymers," Macromolecular Symposia. vol. 233 pp. 42-50 (2006).
Xenidou, and Hadjichristidis, "Synthesis of Model Multigraft Copolymers of Butadiene with Randomly Placed Single and Double Polystyrene Branches," Macromolecules. vol. 31 pp. 5690-5694 (1998).
Yang et al., "I5S Miktoarm Start Block Copolymers: Packing Constraints on Morphology and Discontinuous Chevron Tilt Grain Boundaries," Macromolecules. vol. 34 pp. 9069-9073 (2001).
Yang et al., "Phase Behavior of I2S Single Graft Copolymer/Homopolymer Blends," Macromolecules. vol. 34 pp. 4235-4243 (2001).
Zhu et al., "Effect of Junction Point Functionality on the Lamellar Spacing of Symmetric Miktoarm Star Block Copolymers (PS)n(PI)n," Macromolecules. vol. 36 pp. 5719-5724 (2003).
Zhu et al., "Microphase-Separation of Cyclic Block Copolymers of Styrene and Butadiene and of Their Corresponding Linear Triblock Copolymers," Maromolecules. vol. 36 pp. 148-152 (2003).
Zhu et al., "Morphologies and Mechanical Properties of a Series of Block-Double-Graft Copolymers and Terpolymers," Macromolecules. vol. 35 pp. 5903-5909 (2002).
Cheong et al., "Synthesis and cross-linking of polyisoprene latexes," Polymer, vol. 45, pp. 769-781 (2004).
Cohn et al., "Designing biodegradable multibloack PCL/PLA thermoplastic elastomers," Biomaterials, vol. 26, pp. 2297-2305 (2005).
Datta et al., "Methacrylate/acrylate ABA triblock copolymers by atom transfer radical polymerization; their properties and application as a mediator for organically dispersible gold nanoparticles," Polymer, vol. 50, pp. 3259-3268 (2009).
Dufour et al., "Polar Three-Arm Star Block Copolymer Thermoplastic Elastomers Based on Polyacrylonitrile," Macromolecules, vol. 41, No. 7, pp. 2451-2458 (2008).
Feng et al., "Well-defined graft copolymers:from controlled synthesis to multipurpose applications," Chemical Society Reviews, vol. 40, pp. 1282-1295 (2011).
Frick et al., "Methyl Group Dynamics in Glassy Polyisoprene: A neutron Backscattering Investigation," Macromolecules, vol. 27, No. 4, pp. 974-980 (1994).
Gacal et al., "Anthracene—Maleimide-Based Diels-Alder 'Click Chemistry' as a Novel Routre to Graft Copolymers," Macromolecules, vol. 39, pp. 5330-5536 (2006).
Gamlish et al., "Copolymerization of isoprene and hydroxyl containing monomers by controlled radical and emulsion methods," Polymer Chemistry, vol. 3, pp. 1510-1516 (2012).
Gilman et al., "The analysis of organolithium compounds," J. Organomet. Chem., vol. 2, pp. 447-454 (1964).
Hadjichristidis et al., "Macromolecular architectures by living and controlled/living polymerizations," Prog. Polym. Sci, vol. 31, pp. 1068-1132 (2006).
Hawker et al., "'Living' free radical polymerization of macromonomers: preparation of well defined graft copolymers," Macromolecular Chemistry and Physics, vol. 198, pp. 155-166 (1997).
Ishimoto, et al., "Biobased polymers: synthesis of graft copolymers and comb polymers using lactic acid macromonomer and properties of the product polymers," ACS Publications, Biomacromolecules, vol. 13, pp. 3757-3768 (2012).

(56) References Cited

OTHER PUBLICATIONS

Jeusette et al., "New 'all-acrylate' block copolymers: synthesis and influence of the architecture on the morphology and the mechanical properties," Macromolecules, vol. 40, pp. 1055-1065 (2007).
Ji et al., "Characterization of hydroxyl-end-capped polybutadiene and polystyrene produced by anionic polymerization technique via TLC/MALDI TOF mass spectrometry," Polymer, vol. 43, pp. 7119-7123 (2002).
Jiang et al., "A novel architecture toward third-generation thermoplastic elastomers by a grafting strategy," Macromolecules, vol. 46, pp. 4772-4780 (2013).
Juhari et al., "Star-like poly(n-butyl acrylate)-b-poly($\alpha$-methylene-$\gamma$-butyrolactone) block copolymers for high temperature thermoplastic elastomers applications," Polymer, vol. 51, pp. 4806-4813 (2010).
Kongsinlark et al., "Synthesis of nanosized ethylene-propylene rubber latex via polyisoprene hydrogenation," Journal of Applied Polymer Science, vol. 127, pp. 3622-3632 (2013).
Koromilas et al., "Synthesis and self-association in dilute aqueous solution of hydrophobically modified polycations and polyampholytes based on 4-vinylbenzyl chloride," European Polymer Journal, vol. 54, pp. 39-51 (2014).
Li et al., "Linear-, Cyclic-, and Multiblock Amphiphilic Polyelectrolytes as Surfactants in Emulsion Polymerization: Role of Topological Structure," Macromolecules, vol. 46, pp. 2808-2817 (2013).
Liu et al., "Precision synthesis of w-Branch, End-Functionalized Comb Polystyrenes Using Living Anionic Polymerization and Thiol-Ene 'Click' Chemistry," Macromolecules, vol. 45, pp. 9233-9242 (2012).
Lübke et al., "Imprinted polymers prepared with stoichiometric template-monomer complexes: efficient binding of ampicillin from aqueous solutionis," Macromolecules, vol. 33, pp. 5098-5105 (2000).
Luo et al., "Polystyrene-block-poly(n-butyl acrylate)-block-polystyrene Triblock Copolymer Thermoplastic elastomer Synthesized via RAFT Emulsion Polymerization," Macromolecules, vol. 43, pp. 7472-7481 (2010).
Matyjaszewski et al., "Simple and effective one-pot synthesis of (Meth)Acrylic block copolymers through atom transfer," Journal of Polymer Science Part A: Polymer Chemistry, vol. 38, pp. 2023-2031 (2000).
Minari et al., "Emulsoin polymerization of isoprene. Estimation of the branching exponent with the help of a mathematical model," Journal of Applied Polymer Science, vol. 116, pp. 590-601 (2010).
Moineau et al., "Synthesis and characterization of poly(methyl methacrylate)-block-poly (n-butyl acrylate)-block-poly(methyl methacrylate) Copolymers by two-step controlled radical polymerization (ATRP) catalyzed by NiBr2(PPh3)2. 1," Macromolecules, vol. 32, pp. 8277-8282 (1999).
Neises et al., "Simple method of the estrification of carboxylic acids," Angewandte Chemie International Edition in English, vol. 17, No. 7, pp. 522-524 (1978).
Nese et al., "Synthesis, characterization, and properties of starlike Poly(n-butyl acrylate)-b-poly(methyl methacrylate) block copolymers," Macromolecules, vol. 43, pp. 1227-1235 (2010).
Nicolas et al., "Nanostructure latex particles synthesized by nitroxied-mediated contrlled/living free-radical polymerization in emulsion," Polymer, vol. 48, pp. 7029-7040 (2007).
Paraskeva et al., "Synthesis of an exact graft copolymer of isoprene and styrene with two branches," Journal of Polymer Science Part A: Polymer Chemistry, vol. 38, pp. 931-935 (2000).
Poongavalappil et al., "Study on the influence of electron beam irradiation on the thermal, mechanical, and rheological properties of ethylene-octene copolymer with high comonomer content," Journal of Applied Polymer Science, vol. 128, pp. 3026-3033 (2013).
Pramanik et al., "Organic-inorganic hybrid tinphosphonate material with mesoscopic void spaces: an excellent catalyst for the radical polymerization of styrene," Catalysis Science & Technology, vol. 2, pp. 613-620 (2012).
Prince et al., "Synthetic rubber production," Industrial & Engineering Chemistry, vol. 52, pp. 235-238 (1960).
Quirk et al., "Efficient synthesis of w-(p-Vinylbenzyl)polystyrene by direct fuctionalization of Poly(styryl)lithium with p-Vinylbenzyl chloride in hydrocarbon solvent with lithium 2,3-dimethyl-3-pentoxide," Macromolecules, vol. 39, pp. 1681-1692 (2006).
Rajatapiti et al., "In-Situ Synthesis of PBA-graft-PMMA Copolymers to Be Used as Comatibilizing Agents in PBA/PMMA Composite Latex Particles via the Macromonomer Method," Journal of Macromolecular Science, Part A, vol. 32, pp. 1445-1460 (1995).
Roovers et al., Microheterogeneity in Miscible Blends of 1,2-Polybutadiene and 1,4-Polyisoprene, Macromolecules vol. 25, No. 13, pp. 3454-3461 (1992).
Singh et al., "Effect of molecular weight on the mechanical and electrical properties of block copolymer electrolytes," Macromolecules, vol. 40, pp. 4578-4585 (2007).
Spontak et al., "Thermoplastic elastomers:fundamentals and applications," Current Opinion in Colloid & Interface Science, vol. 5, pp. 334-341 (2000).
Suppaibulsuk et al., "Synthesis of styrene-g-polyisoprene nanoparticles by emulsion polymerization and its effect on properties of polyisoprene composites," Polymers for Advanced Technologies, vol. 23, pp. 1473-1483 (2012).
Theryo et al., "Tough Polylactide Graft Copolymers," Macromolecules, vol. 43, pp. 7394-7397 (2010).
Uhrig et al., "Synthesis of well-defined multigraft copolymers," Polymer Chemistry, vol. 2, pp. 69-76 (2011).
Uhrig et al., "Multigraft copolymer superelastomers: synthesis morphology, and properties," European Polymer Journal, vol. 47, pp. 560-568 (2011).
Wang et al., "Synthesis and Characterization of Comb and Centipede Multigraft Copolymers PnBa-g-PS with High Molecular Weight Using Miniemulsion Polymerization" Macromolecules, vol. 47, pp. 7284-7295 (2014).
Wang et al., Synthesis of poly (methyl methacrylate)-b-polystyrene with high molecular weight by DPE seeded emulsion polymerization and its application in proton exchange membrane, Journal of Colloid and Interface Science, vol. 406, pp. 154-164 (2013).
Wei et al., "Styrene-Butadiene-Styrene Triblock Copolymer Latex via Reversible Addition-Fragmentation Chain Transfer Miniemulsion Polymerization," Industrial & Engineering Chemistry Research, vol. 51, pp. 15530-15535 (2012).
Wisse et al., "Segmental Orientation in Well-Defined Thermoplastic Elastomers Containing Supramolecular Fillers," Macromolecules, vol. 42, pp. 524-530 (2008).
Wu et al., "Investigation of Thermodynamic Properties of SIS, SEBS, and Naphthenic Oil by Inverse Gas Chromatography," Journal of Elastomers and Plastics, vol. 43, pp. 369-386 (2011).
Yongxin et al., "Deformation Behavior of Sphere-Forming Trifunctional Multigraft Copolymer," Macromolecules. vol. 41 pp. 4565-4568 (2008).
Yoshizaki et al., "Transport Coefficients of Helical Wormlike Chains. 4. Intrinsic Viscosity of the Touched-Bead Model," Macromolecules, 21, pp. 165-171 (1988).
Zhang et al., "Synthesis and surface properties of PDMS-containing latexes by emulsion polymerization using AIBN as the initiator," European Polymer Journal, vol. 49, pp. 2327-2333.
Notification Concerning Transmittal of Copy of International Preliminary Report on Patentability corresponding to International application No. PCT/US2015/036727 dated Dec. 29, 2016.
Notification of Transmittal of the International Search Report and the Written Opinion of the International Searching Authority corresponding to International application No. PCT/US2015/036727 dated Nov. 26, 2015.
Wang et al., "Synthesis and Characterization of Graft Copolymers Poly(isoprene-g-styrene) of High Molecular Weight by a Combination of Anionic Polymerization and Emulsion Polymerization,"Ind. Eng., Chem. Res., vol. 54(4), pp. 1292-1300 (Jan. 14, 2015).

\* cited by examiner

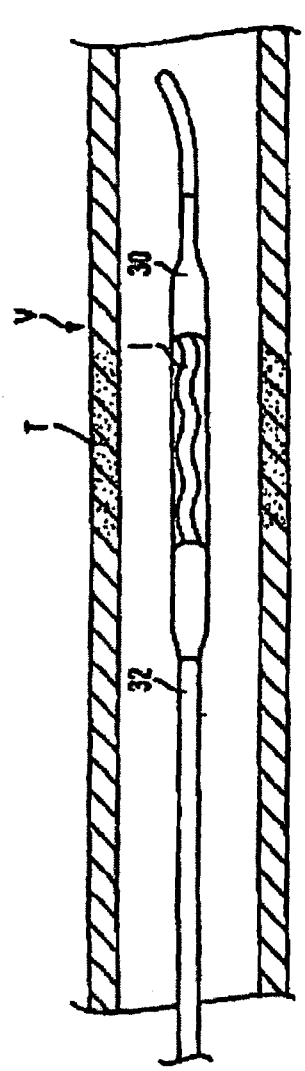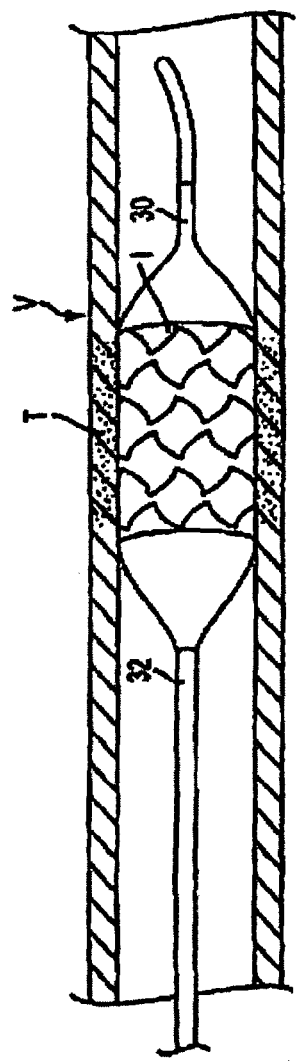
FIG. 13A
FIG. 13B

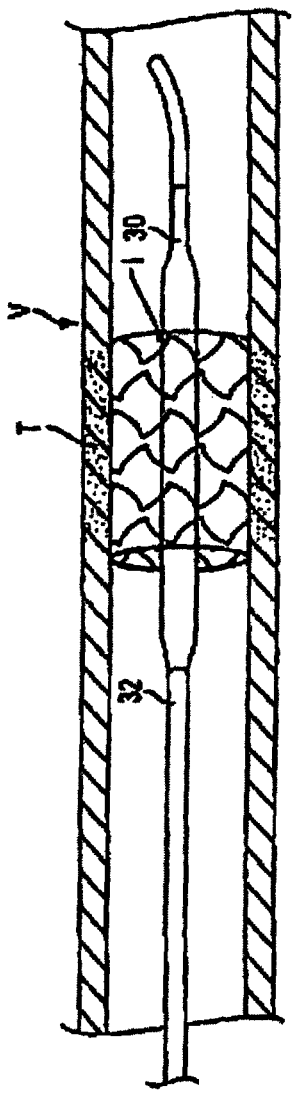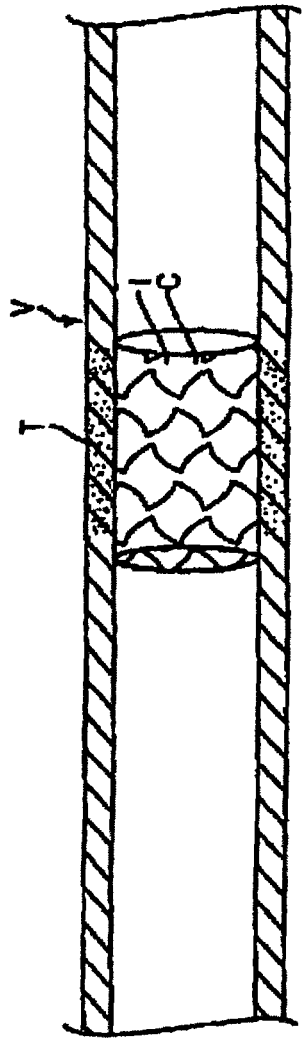
FIG. 13C
FIG. 13D

Tensile characteristics of random multigraft copolymer strain at break

| | $\varepsilon_B$ [%] |
|---|---|
| MG-4-15-4/5 | 1783 ± 11 |
| MG-4-15-7/8 | 1445 ± 32 |
| MG-4-20-6 | 1344 ± 34.7 | tensile strength

| | $\sigma_B$ [N/mm²] |
|---|---|
| MG-4-15-4/5 | 5.82 ± 0.16 |
| MG-4-15-7/8 | 9.87 ± 0.66 |
| MG-4-20-6 | 10.6 ± 0.98 | elastic modulus

| | E [N/mm²] |
|---|---|
| MG-4-15-4/5 | 3 ± 0.29 |
| MG-4-15-7/8 | 4.21 ± 0.08 |
| MG-4-20-6 | 6.58 ± 0.78 |

MULTIGRAFT COPOLYMERS AS SUPERELASTOMERS

CROSS-REFERENCE TO RELATED APPLICATIONS

This application is a 35 U.S.C. §371 national stage application of International Patent Application No. PCT/US2011/054345 filed on Sep. 30, 2011, which claims the benefit of priority to U.S. Provisional Patent Application No. 61/389,025 filed on Oct. 1, 2010, the disclosures of which are hereby incorporated by reference.

TECHNICAL FIELD

Elastomers comprising multigraft copolymers having randomly spaced branch points, for example comprising a polydiene backbone and randomly spaced polystyrene grafts, are described. Also described are methods of synthesizing and characterizing the copolymers. The copolymers can be used as superelastomers, for example, in adhesives and/or as components in a variety of products, including medical implants.

BACKGROUND

Thermoplastic elastomers (TPEs) represent an important segment of the worldwide elastomer market due to their combination of mechanical properties comparable to vulcanized rubbers and straightforward processing similar to that of thermoplastics. See Legge et al., Thermoplastic Elastomers, Munich: Hanser, 1987. TPEs are also of interest because of their capacity to self-assemble to form ordered phase separated structures having nanoscale dimensions, with morphologies and properties tunable by controlling the volume fractions of hard and soft segments. See Rader, C. P., in Modern Plastics Encyclopedia, Volume 72, New York: McGraw-Hill, 1996.

Linear ABA triblock copolymers, including styrenic block copolymers (SBC), are often usable as TPEs. The SBCs include, for example, the SIS and SBS triblock copolymers, where S represents glassy polystyrene (PS) end-blocks and I and B represent rubbery polyisoprene (PI) and polybutadiene (PBD) mid-blocks, respectively. Some of these copolymers are sold under the trade name KRATON™ (Kraton Polymers, Houston, Tex., United States of America). For these block copolymers, the morphology formed, and thus the mechanical properties, are directly linked to the volume fractions of the two components.

Star block copolymers, e.g., star polymers where each arm is a block copolymer, having PS outer blocks and PI inner blocks, have been reported as having improved tensile strength relative to linear triblocks of comparable composition and segment molecular weights. See Bi and Fetters, *Macromolecules*, 9, 732-742 (1976). Commercial star block copolymers based on S/I and S/B compositions have been commercialized by companies such as the Phillips Petroleum Company (now part of ConocoPhillips Company, Houston, Tex., United States of America), and BASF (Ludwigshafen, Germany).

Graft copolymers comprising PI backbones and regularly spaced PS side chains attached to the backbone at branch points have also been shown to have elastomeric properties. See, e.g., Uhrig and Mays, *Macromolecules*, 35, 7182-7190 (2002); and Mays et al., *Macromol. Symp.*, 215, 111-126 (2004). However, the synthesis of regular spaced copolymers can be challenging. See Uhrig and Mays, *Macromolecules*, 35, 7182-7190 (2002).

Accordingly, there is need in the art for additional elastomeric polymers and materials that can be produced therefrom, that can be synthesized easily and at low cost. There is also a continuing need for elastomeric polymers that have mechanical properties that can be readily fine-tuned particular end uses.

SUMMARY OF THE INVENTION

In some embodiments, the presently disclosed subject matter provides a thermoplastic elastomer composition comprising a random multigraft copolymer comprising a rubbery polymeric backbone and a plurality of glassy polymeric grafts, wherein each of the plurality of glassy polymeric grafts is attached to the rubbery polymeric backbone at one of a plurality of randomly spaced branch points. In some embodiments, the composition further comprises at least one additional component selected from the group comprising an organic filler, an inorganic filler, a wax, a tackifier, a plasticizer, an anti-oxidant, a stabilizer, a decorative agent, a biocide, a flame retardant, an anti-static agent, a therapeutic agent and combinations thereof. In some embodiments, the decorative agent is a pigment or a dye.

In some embodiments, the random multigraft copolymer has a residual strain of about 55% or less at an applied strain of about 500% or more. In some embodiments, the random multigraft copolymer has a residual strain of about 40% or less at an applied strain of about 300% or more.

In some embodiments, the random multigraft copolymer has a strain at break of 1200% or greater. In some embodiments, the random multigraft copolymer has a strain at break of at least 1500%.

In some embodiments, the random multigraft copolymer has a percent strain at break that increases linearly with the number of branch points. In some embodiments, the random multigraft copolymer comprises an architecture selected from the group comprising a trifunctional comb architecture, a tetrafunctional centipede architecture, and a hexafunctional barbwire architecture.

In some embodiments, the rubbery polymeric backbone comprises a polymeric material selected from the group comprising polyisoprene, hydrogenated polyisoprene, polybutadiene, hydrogenated polybutadiene, polyisobutylene, butyl rubber, poly(butadiene-co-acrylonitrile), a silicone rubber (e.g., polydimethylsiloxane or another siloxane polymer), acrylic rubber, polychloroprene, ethylene propylene copolymer, ethylene/acrylic elastomer, urethane rubber, and combinations thereof. In some embodiments, the glassy polymeric grafts comprise a polymer selected from the group comprising polystyrene, hydrogenated polystyrene, poly(α-methylstyrene) or another glassy styrenic polymer or hydrogenated derivative thereof, polyethylene, urethane hard domain, polyester, polymethylmethacrylate or another glassy acrylic polymer, polyvinyl chloride, poly(vinylpyridine), polycarbonate, nylon, polyethylene terephthalate, polycyclohexadiene, hydrogenated polycyclohexadiene, and combinations thereof. In some embodiments, the rubbery polymeric material is polyisoprene and the glassy polymeric material is polystyrene.

In some embodiments, the random multigraft copolymer has a volume fraction of glassy polymeric grafts of between about 10% and about 50%. In some embodiments, the volume fraction of glassy polymeric grafts is between about 14% and about 26%. In some embodiments, the random multigraft copolymer comprises at least three branch points.

In some embodiments, the random multigraft copolymer has a molecular weight of between about 400,000 and about 600,000.

In some embodiments, the presently disclosed subject matter provides a fabricated article comprising a thermoplastic elastomer composition comprising a random multigraft copolymer comprising a rubbery polymeric backbone and a plurality of glassy polymeric grafts, wherein each of the plurality of glassy polymeric grafts is attached to the rubbery polymeric backbone at one of a plurality of randomly spaced branch points. In some embodiments, the fabricated article is prepared by injection molding, compression molding, extrusion, or calendaring.

In some embodiments, the fabricated article is selected from the group comprising automotive interior or exterior parts, shoe soles or other shoe parts, elastic waistbands, diaper backings or attachments, adhesive tapes, membranes, balloons, bags, tubing, roofing tiles, medical devices, and electronic wiring coatings or other electronic device components. In some embodiments, the fabricated article is a medical device selected from a balloon catheter and a stent. In some embodiments, the article is a balloon catheter, wherein at least the inflatable portion of the balloon catheter comprises the thermoplastic elastomer composition.

In some embodiments, the presently disclosed subject matter provides an adhesive comprising: a random multigraft copolymer comprising a rubbery polymeric backbone and a plurality of glassy polymeric grafts, wherein each of the plurality of glassy polymeric grafts is attached to the rubbery polymeric backbone at one of a plurality of randomly spaced branch points; and a tackifier. In some embodiments, the adhesive is a pressure sensitive adhesive or a hot melt adhesive.

In some embodiments, the tackifier is selected from the group comprising rosins and derivatives thereof, terpenes, modified terpenes, an aliphatic resin, a cycloaliphatic resin, an aromatic resin, a hydrogenated hydrocarbon resin, a terpene-phenol resin, and mixtures thereof. In some embodiments, the adhesive further comprises one or more additives selected from the group comprising waxes, plasticizers, anti-oxidants, stabilizers, decorative agents, biocides, flame retardants, anti-static agents, and fillers. In some embodiments, the decorative agent is a pigment, a dye or glitter.

In some embodiments, the presently disclosed subject matter provides a coated object comprising a coating layer comprising a random graft copolymer, wherein the random multigraft copolymer comprises a rubbery polymeric backbone and a plurality of glassy polymeric grafts, wherein each of the plurality of glassy polymeric grafts is attached to the rubbery polymeric backbone at one of a plurality of randomly spaced branch points, wherein the coating layer covers at least a portion of a surface of a wood, ceramic, glass, carbon fiber, metal, metallic, leather, fabric, stone, or plastic object. In some embodiments, the object is selected from the group comprising an article of clothing, an eating/cooking utensil, a medical implant, a medical/surgical tool, and an electronic device.

In some embodiments, the object is a medical implant or a medical/surgical tool and the coating layer further comprises a therapeutic agent additive selected from the group comprising a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, a retinoid, a flavonoid, a carotenoid, a lipid improving agent, a DNA synthesis inhibitor, a tyrosine kinase inhibitor, an antiplatelet, a vascular smooth muscle antiproliferative agent, an anti-inflammatory agent, an interferon, and a NO production accelerator. In some embodiments, the coated object comprises a stent, wherein the stent comprises metal or metallic wire mesh or a metal or metallic coil having a cylindrical shape, wherein the wire mesh or coil is covered by the coating layer.

It is an object of the presently disclosed subject matter to provide random multigraft copolymers having elastomeric properties and articles comprising the copolymers.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 13A is a schematic drawing showing a balloon catheter assembly at a target site in a vessel per U.S. Pat. No. 7,794,491.

FIG. 13B is a schematic drawing showing a balloon catheter assembly at a target site in a vessel per U.S. Pat. No. 7,794,491, with the balloon inflated and the stent radially expanded.

FIG. 13C is a schematic drawing showing a balloon catheter assembly at a target site in a vessel per U.S. Pat. No. 7,794,491, with the balloon deflated and the stent expanded.

FIG. 13D is a schematic drawing showing a stent implanted at a target site in a vessel per U.S. Pat. No. 7,794,491.

DETAILED DESCRIPTION OF THE DISCLOSED EMBODIMENTS

Figure 1A:
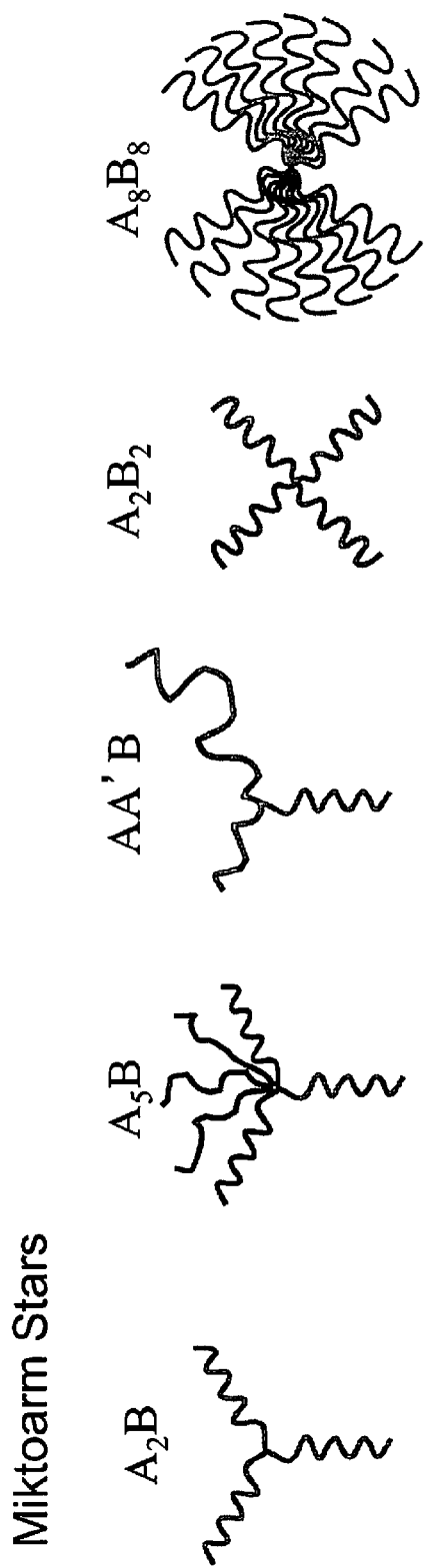
FIG. 1A is a schematic drawing showing the molecular architecture of miktoarm star copolymers comprising two types of block material, A and B.

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "an additive" includes a plurality of such additives, and so forth.

Unless otherwise indicated, all numbers expressing quantities of size, number of metal ions, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size, weight, concentration, or percentage is meant to encompass variations of, in some embodiments ±20%, in some embodiments ±10%, in some embodiments ±5%, in some embodiments ±1%, and in some embodiments ±0.1% from the specified amount, as such variations are appropriate to perform the disclosed methods.

The term "and/or" when used to describe two or more activities, conditions, or outcomes refers to situations wherein both of the listed conditions are included or wherein only one of the two listed conditions are included.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of" and "consisting essentially of", where one of these three terms is used herein, the presently disclosed and claimed subject matter can include the use of either of the other two terms.

As used herein, the term "anionic polymerization" refers to an ionic polymerization in which the kinetic chain carriers are anions. Accordingly, an anionic polymerization reaction is a chain reaction in which the growth of the polymer chain proceeds by reaction(s) between a monomer(s) and a reactive site(s) on the polymer chain with regeneration of the reactive site(s) at the end of each growth step. Anionic polymerization typically takes place with monomers comprising electron-withdrawing groups, such as nitrile, carboxyl, phenyl, and vinyl, or with monomers that can stabilize the anions through resonance. These polymerizations are initiated by nucleophilic addition to the double bond of the monomer, wherein the initiator comprises an anion, such as hydroxide, alkoxides, cyanide, or a carbanion. In some embodiments, the carbanion is generated from an organometallic species, such as an alkyl lithium, e.g., butyl lithium, or a Grignard reagent. Anionic polymerization typically is used to produce macromolecules from monomers that contain a carbon-carbon double bond, such as styrene and/or butadiene. Such reactions are referred to as anionic vinyl polymerization.

As used herein, a "monomer" refers to a molecule that can undergo polymerization, thereby contributing constitutional units, i.e., an atom or group of atoms, to the essential structure of a macromolecule.

As used herein, a "macromolecule" refers to a molecule of high relative molecular mass, the structure of which comprises the multiple repetition of units derived from molecules of low relative molecular mass, e.g., monomers and/or oligomers.

An "oligomer" refers to a molecule of intermediate relative molecular mass, the structure of which comprises a small plurality of units derived from molecules of lower relative molecular mass.

A "polymer" refers to a substance composed of macromolecules.

A "copolymer" refers to a polymer derived from more than one species of monomer.

As used herein, a "block macromolecule" refers to a macromolecule that comprises blocks in a linear sequence. A "block" refers to a portion of a macromolecule that has at least one feature that is not present in the adjacent portions of the macromolecule. A "block copolymer" refers to a copolymer in which adjacent blocks are constitutionally different, i.e., each of these blocks comprises constitutional units derived from different characteristic species of monomer or with different composition or sequence distribution of constitutional units.

For example, a diblock copolymer of polybutadiene and polystyrene is referred to as polybutadiene-block-polystyrene. Such a copolymer is referred to generically as an "AB block copolymer" or an "AB diblock copolymer". Likewise, a triblock copolymer can be represented as "ABA." Other types of block polymers exist, such as multiblock copolymers of the $(AB)_n$ type, ABC block polymers comprising three different blocks, and star block polymers, which have a central point with three or more arms, each of which is in the form of a block copolymer, usually of the AB type.

As used herein, a "graft macromolecule" or "graft copolymer" refers to a macromolecule comprising one or more species of block connected to the main chain as side chains, wherein the side chains comprise constitutional or configurational features that differ from those in the main chain.

A "branch point" (or "junction point") refers to a point on a chain at which a branch is attached. A "branch," also referred to as a "side chain" or "pendant chain," is an oligomeric or polymeric offshoot from a macromolecule chain. An oligomeric branch can be termed a "short chain branch," whereas a polymeric branch can be termed a "long chain branch."

A "chain" refers to the whole or part of a macromolecule, an oligomer, or a block comprising a linear or branched sequence of constitutional units between two boundary constitutional units, wherein the two boundary constitutional units can comprise an end group, a branch point, or combinations thereof.

A "main chain" or "backbone" refers to a linear chain from which all other chains are regarded as being pendant.

A "side chain" refers to a linear chain which is attached to a main chain at a branch point.

An "end group" refers to a constitutional unit that comprises the extremity of a macromolecule or oligomer and, by definition, is attached to only one constitutional unit of a macromolecule or oligomer.

A "comb macromolecule" refers to a macromolecule comprising a main chain with multiple trifunctional branch points from each of which a linear side chain emanates.

A "star polymer" refers to a polymer comprising a macromolecule comprising a single branch point from which a plurality of linear chains (or arms) emanate. A star polymer or macromolecule with "n" linear chains emanating from the branch point is referred to as an "n-star polymer." If the linear chains of a star polymer are identical with respect to constitution and degree of polymerization, the macromolecule is referred to as a "regular star macromolecule." If different arms of a star polymer comprise different monomeric units, the macromolecule is referred to as a "variegated star polymer."

A "miktoarm star polymer" refers to a star polymer comprising chemically different (i.e., "mixed") arms, thereby producing a star polymer having the characteristic of chemical asymmetry.

II. Multigraft Copolymers

Figure 1B:
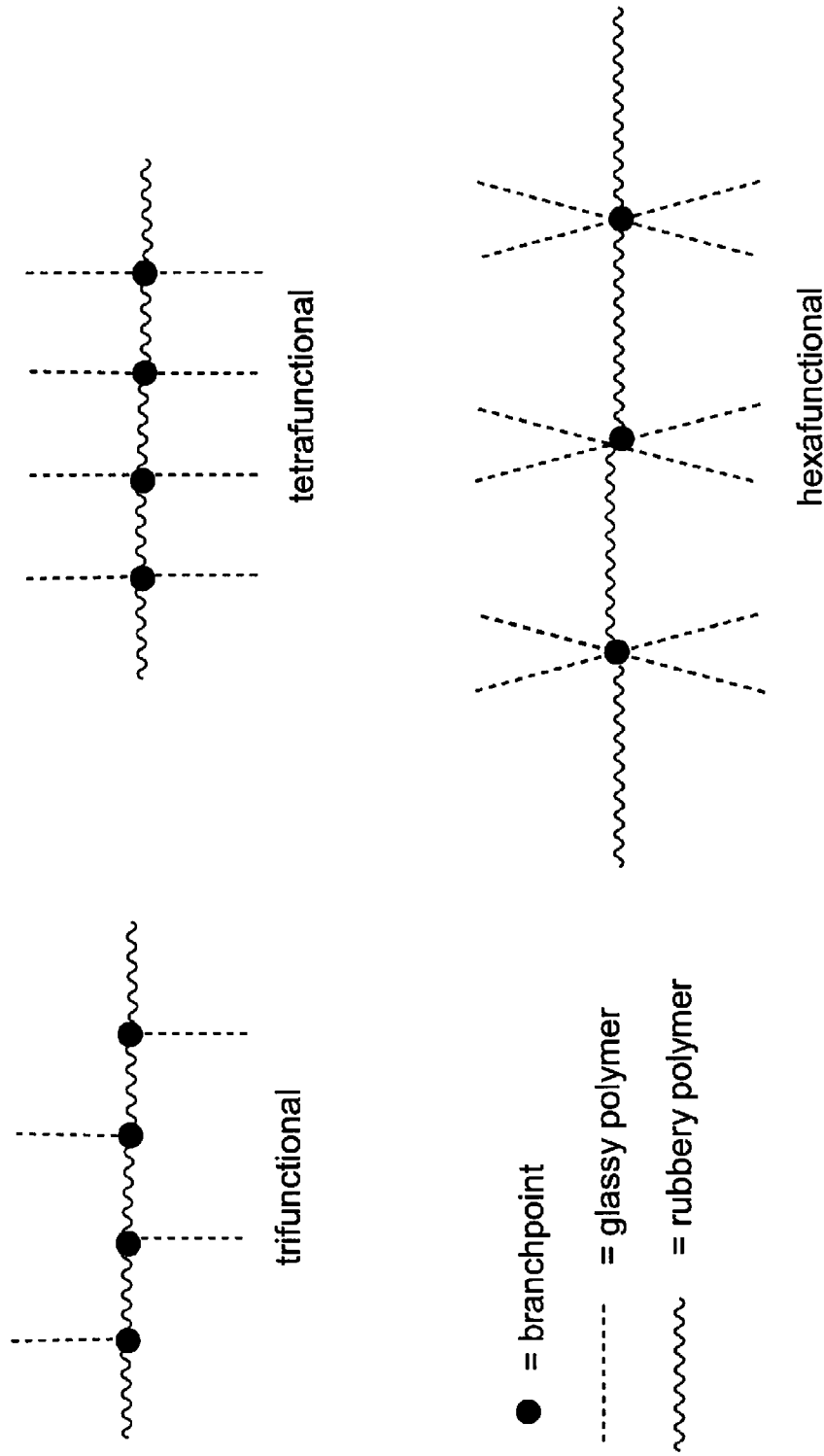
FIG. 1B is a schematic drawing showing the molecular architectures of regular multigraft copolymers having rubbery polymer backbones and glassy polymer side chains. The copolymer architectures include a trifunctional "comb" architecture, a tetrafunctional "centipede" architecture, and a hexafunctional "barbwire" architecture.

FIG. 1B shows comb, centipede and barbwire regular multigraft copolymers where the branch points are evenly spaced along the backbone, i.e., "regular" multigraft copolymers. In the regular multigraft copolymers, the backbone chain segment between each branch point is the same length. Elastomeric properties of certain regular multigraft copolymers have been described previously. See e.g., Zhu et al., Macromolecules, 39, 4428-4436 (2006). Without being bound to any one theory, the elastomeric properties of multigraft copolymers comprising rubbery backbones and glassy (or semi-crystalline) grafts are believed to be related to the backbone imparting stretchability, while the grafts impart elastic recovery. The multigraft copolymers show improved strain at break in comparison to other TPEs (e.g., triblock copolymers), believed to be due to enhanced load transfer between the rubbery matrix and the many dispersed glassy domains.

Figure 1C:
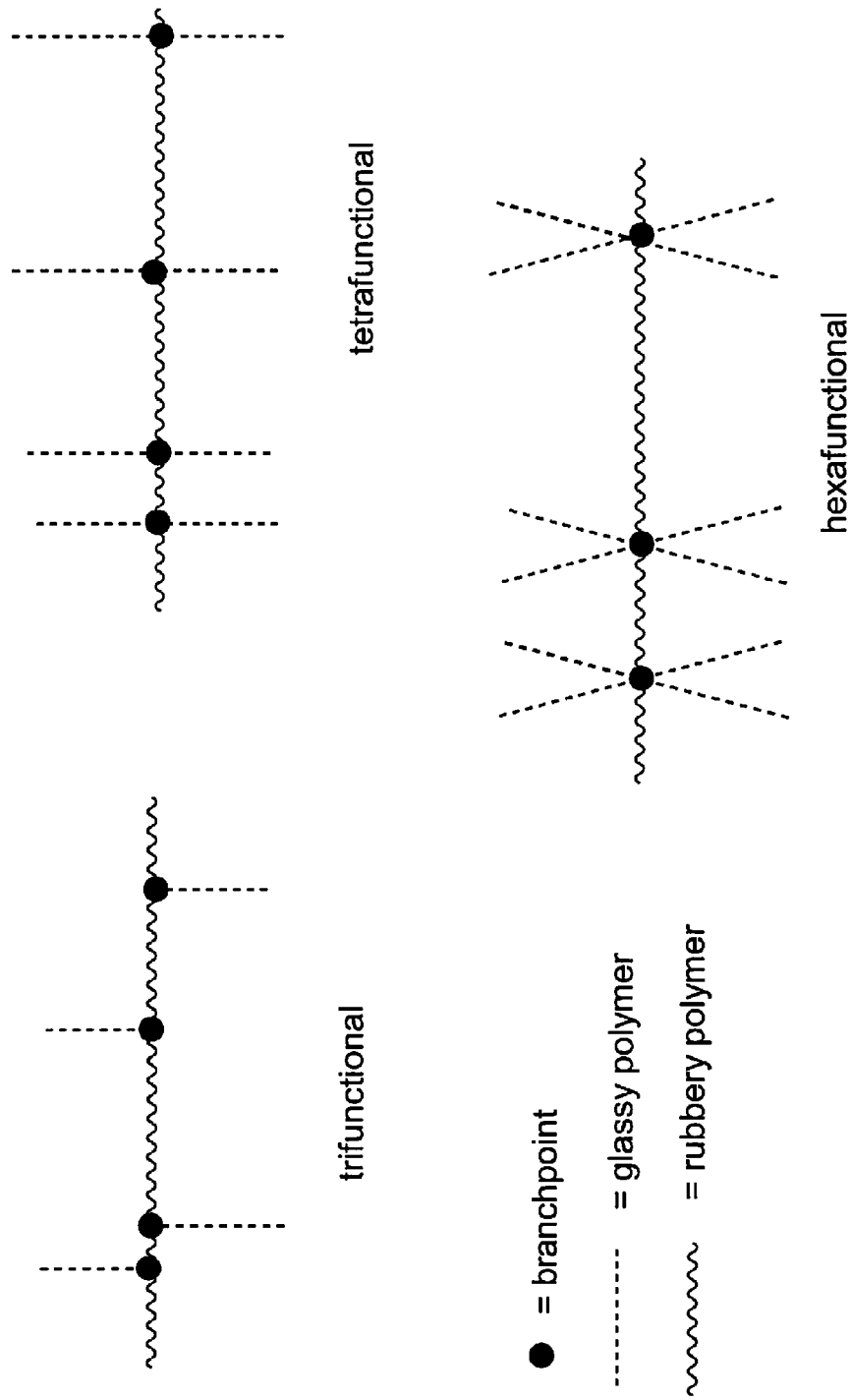
FIG. 1C is a schematic drawing showing the molecular architecture of random multigraft copolymers having rubbery polymer backbones and glassy polymer side chains. The copolymer architectures include a trifunctional "comb" architecture, a tetrafunctional "centipede" architecture, and a hexafunctional "barbwire" architecture.
Figure 2A:
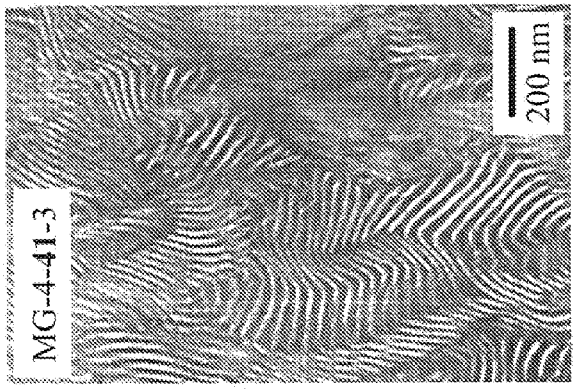
FIG. 2A is a theoretical phase diagram for a linear diblock or triblock copolymers comprising rubbery and glassy components, which can also apply to regular tetrafunctional multigraft copolymers. The volume fraction of the glassy component is plotted on the x axis. For samples having a roughly equal volume of the two components, a lamellar (L) morphology is formed. H stands for hexagonally packed cylindrical morphology.
Figure 2B:
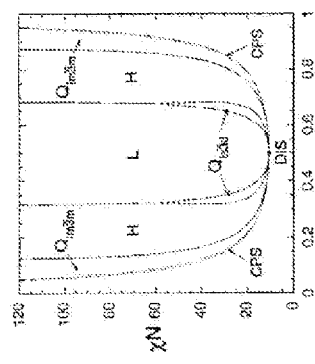
FIG. 2B is a transmission electron micrograph (TEM) image of a regular tetrafunctional multigraft copolymer with a PI backbone and PS grafts. In the TEM image, the PS phase appears light and the PI phase appears dark. The copolymer comprises 14 volume % PS and an average of 2.5 branch points. A morphology of dispersed spheres of PS in a PI matrix is formed.
Figure 2C:
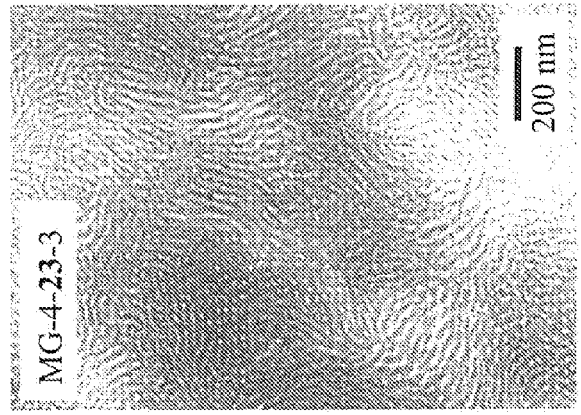
FIG. 2C is a transmission electron micrograph (TEM) image of a regular tetrafunctional multigraft copolymer with a PI backbone and PS grafts. In the TEM image, the PS phase appears light and the PI phase appears dark. The copolymer comprises 23 volume % PS and an average of 3 branch points. A hexagonally packed cylindrical morphology is formed.
Figure 2D:
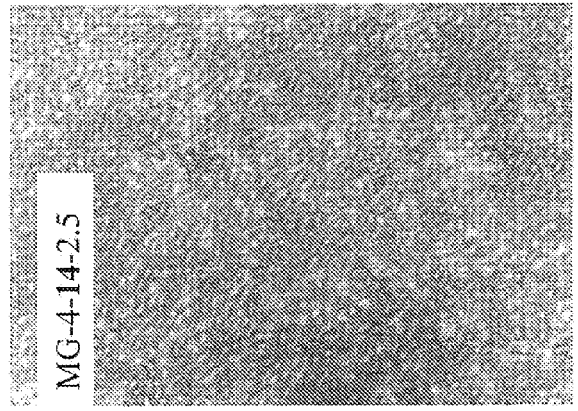
FIG. 2D is a transmission electron micrograph (TEM) image of a regular tetrafunctional multigraft copolymer with a PI backbone and PS grafts. In the TEM image, the PS phase appears light and the PI phase appears dark. The copolymer comprises 41 volume % PS and an average of 3 branch points. A lamellar morphology is formed.

FIG. 1C shows comb, centipede and barbwire copolymers where the branch points are randomly spaced along the backbone, wherein the backbone chain segments between the branch points have different lengths. In one aspect of the presently disclosed subject matter, it is believed that the random placement of the grafts does not negatively affect the elastic properties of the copolymers. Rather, it is believed that the random multigraft copolymers can provide elastic properties similar to regular multigraft copolymers and/or superior to block copolymer TPEs traditionally used as elastomers. Since they can be synthesized cost-effectively and easily on a large scale, it is further believed that the random multigraft copolymer can be readily provided for numerous applications.

II.A. Graft Copolymer Synthesis

Various synthetic routes can be used to provide multigraft copolymers. For example, multigraft copolymers can be prepared by metallation of a polydiene backbone (referred to as a "grafting from strategy"). See Harada et al., J. Polym Sci. Part A-1, 6, 559-573 (1968); Minoura and Harada, J. Poly. Sci. Part A-1, 7, 3-14 (1969); and Tate et al., J. Poly. Sci. Part A-1, 9, 139-145 (1971). While original metallation syntheses were reported to lead to degradation of the polydiene backbone, milder metallation conditions can be employed to minimize polymer degradation. See Falk et al., Rubber Chem. Technol., 46, 1044-1054 (1973). PI-graft-PS multigraft copolymers have been prepared using mild metallation conditions in concert with high vacuum line techniques and a vessel equipped with an optical cell to improve control during the synthesis. See Hadjichristidis et al., J. Polym. Sci. Polym. Phys. Ed., 16, 851-858 (1978); Hadjichristidis et al., J. Polym. Sci. Part A: Polym. Chem., 38, 3211-3234 (2000); and Uhrig and Mays, J. Polym. Sci. Part A: Polym. Chem., 43, 6179-6222 (2005). Scheme 1 shows a route to a graft copolymer via mild metallation using sec-butyl lithium and tetramethylethylenediamine (TMEDA) to create anionic sites on a polydiene backbone chain that can serve as initiation sites for the growth of polystyrene side chains. While some homopolystyrene can be produced, it can be removed by fractionation.

Scheme 1. Synthesis of Graft Copolymer Using a "Grafting From" Stategy and Mild Metallation Conditions.

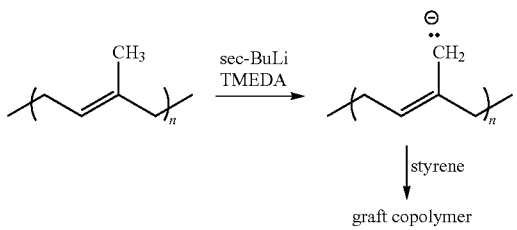

Graft copolymers can also be synthesized by a "grafting to" approach, involving the use of hydrosilation chemistry to introduce chlorosilane functionality onto the backbone chain as shown below in Scheme 2. The chlorosilane groups can then be reacted with pre-prepared side chains. See Cameron and Qureshi, Makromol. Chem., Rapid Commun., 2, 287-291 (1981). The "grafting to" approach allows for characterization of both the backbone and side chains prior to the grafting reaction. Further, the reaction of the polystyrene anions with chlorosilane groups is generally free of side reactions. This strategy can be extended so that each branch point can have two side chains (i.e., tetrafunctional branch points) by using dichloromethylsilane in the hydrosilation step. See Xenidou and Hadjichristidis, *Macromolecules,* 31, 5690-5694 (1998).

Scheme 2. Functionalization of a Polydiene as Part of a "Grafting To" Strategy for the Synthesis of a Graft Copolymer

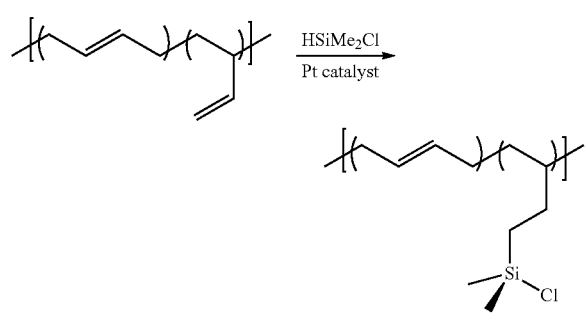

In situ synthesis and polymerization of macromonomers has also been shown to be an effective strategy for the synthesis of comb and other graft polymers. See Knauss et al., *Macromolecules,* 33, 3557-3568 (2000); Al-Muallem and Knauss, *J. Polym. Sci. Polym. Chem. Ed.,* 39, 3547-3555 (2001); and Pantazis et al., *Macromolecules,* 36, 3783-3785 (2003). For example, copolymerization of polystyrene macromonomers with diene monomers in the presence of randomizers can provide multigraft copolymers having polydiene backbones with randomly placed tetrafunctional and pentafunctional multigrafts. See Driva et al., *J. Polym. Sci. Part A: Polym. Chem.,* 43, 4070-4078 (2005); and Nikopoulou et al., *J. Polym. Sci. Part A: Polym. Chem.,* 45, 3513-3523 (2007). Randomizers can include, for example, potassium alkoxides and other alkali metal oxides. The synthesis of polybutadiene-graft-polystyrene "doubly tailed" multigrafts is shown below in Scheme 3.

Scheme 3. Synthesis of "Doubly Tailed" Multigraft Copolymers

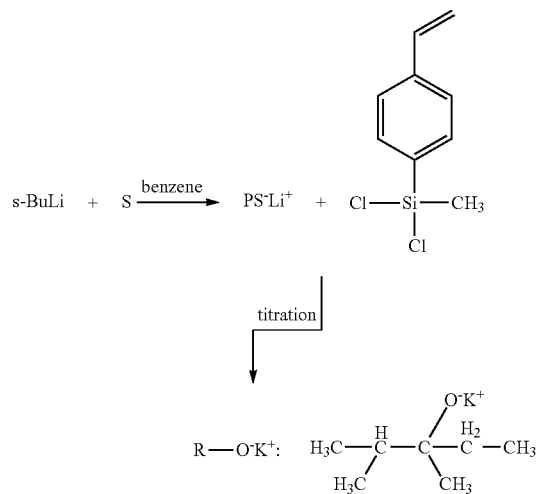

As described in U.S. Pat. No. 7,619,036, incorporated herein by reference in its entirety, multigraft copolymers having regularly spaced branch points and a controlled number of branch points can be prepared using a macromonomer end-linking reaction scheme. Polymer backbone segments (for example, polybutadiene (PBD) or PI) for multigraft copolymers can be made using the dilithium initiator:

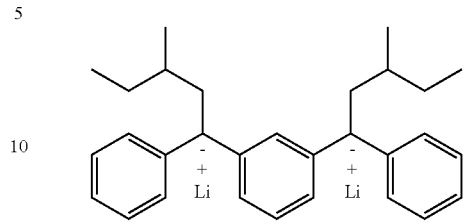

Difunctional Lithium Initiator (DLi)

Use of the difunctional initiator results in the formation of a polymer with reactive anions at both ends of the chain:

DLi+BD→LiPBDLi.

Polymer branches (for example, PS) can be made using a monofunctional anionic initiator, e.g., sec-BuLi:

sec-BuLi+S→PSLi.

Accordingly, multigraft polymers comprising a "comb" architecture can be synthesized via the following reaction scheme:

PSLi+MeSiCl$_3$ (large excess)→(PS)(Me)SiCl$_2$+Me-SiCl$_3$↑(PS)(Me)SiCl$_2$+LiPBDLi (small excess)
→PBD[Si(PS)(Me)]$_n$PBD.

Multigraft polymers comprising a "centipede" architecture can be synthesized via the following reaction scheme:

PSLi+SiCl$_4$ (vacuum titration)→(PS)$_2$SiCl$_2$ (PS)$_2$SiCl$_2$+LiPBDLi→PBD[Si(PS)$_2$]$_n$PBD.

During the synthesis of graft copolymers, samples of polymer segments can be taken during the reactions (whenever possible) to allow for the independent characterization of the precursor segments and the final block copolymers by absolute molecular weight methods such as osmometry, matrix assisted laser desorption ionization time-of-flight mass spectrometry (MALDI-TOF-MS), and light scattering, as well as by gel permeation chromatography (GPC), nuclear magnetic resonance (NMR) spectrometry, and infrared (IR) spectrometry.

II.B. Morphology and Mechanical Properties

Variations in the molecular architecture of graft copolymers can be manipulated to control their nano-scale structure (morphology) and their ability to form long-range order during self-assembly. To provide a desired performance, the size, shape and symmetry, and overall volume fraction of different types of domains can be controlled independently. This independent control is not possible with conventional linear AB diblock copolymers and ABA triblock copolymers for which the nanophase separated morphology which forms (e.g., spheres, cylinders, cubic bicontinuous gyroid, or lamella) is tied directly to the relative volume fractions of the two block materials.

One way to uncouple block copolymer morphology from its rigid dependence on component volume fractions is to vary molecular architecture. By way of example, for mixed arm star architectures such as the A$_2$B shown in FIG. 1A, the asymmetry factor is: $\epsilon=(n_A/n_B)(\zeta_A/\zeta_B)$, wherein $(n_A/n_B)$ is the ratio of arm numbers of the two block types and represents the asymmetry due to the architecture and the conformational asymmetry between the two block materials is expressed by the ratio, $(\zeta_A/\zeta_B)$, wherein $\zeta_i$ is the ratio of segmental volume to the square of statistical segment length for the block material i.

Methods to determine the architectural asymmetry part of a generalized asymmetry parameter for any of the various graft copolymer architectures encountered have been developed. Further, these methods have been tested with extensive morphological studies of model star and graft shaped block copolymers. Also, complex graft copolymer architectures with regular multiple grafting points (e.g., FIG. 1B) can be understood morphologically by analogy to fundamental building blocks defined as the average structure per junction.

This fundamental component of a larger graft molecular architecture is referred to as the "constituting block copolymer." For a graft copolymer with a backbone of A and blocks of B joined to the backbone at trifunctional branch points, the constituting block copolymer is an $A_2B$ single graft copolymer.

Figure 3:
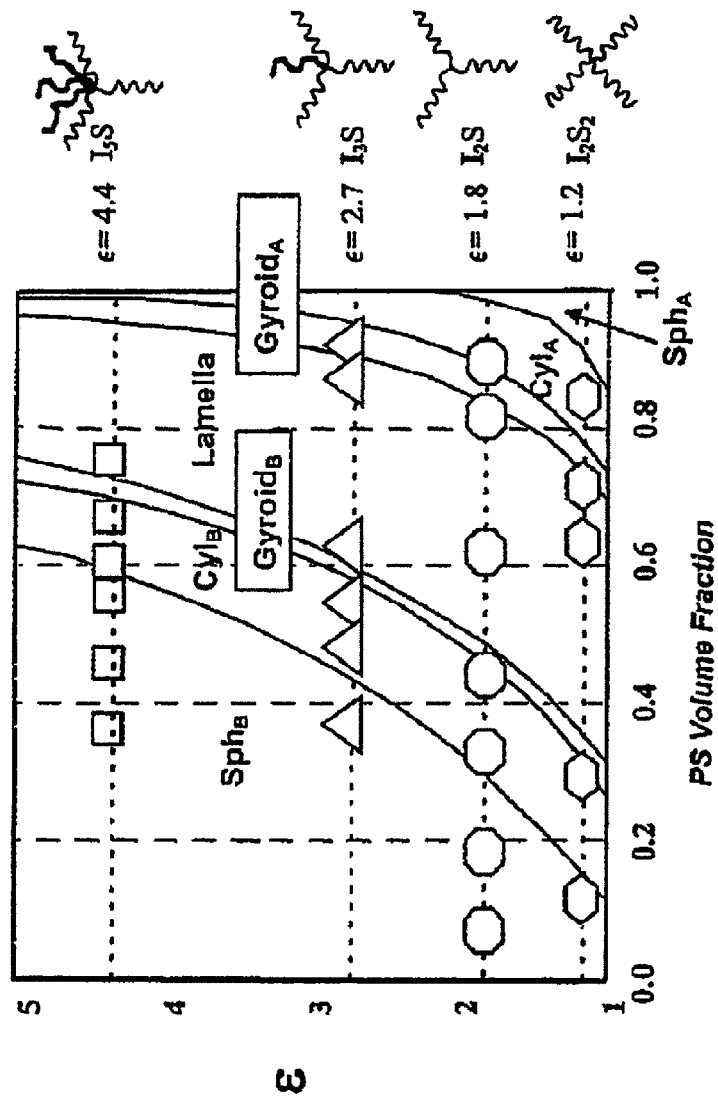
FIG. 3 is a miktoarm star morphology diagram based on experimental results. Epsilon ($\epsilon$) is a parameter that describes the level of architectural asymmetry.
Figure 4:
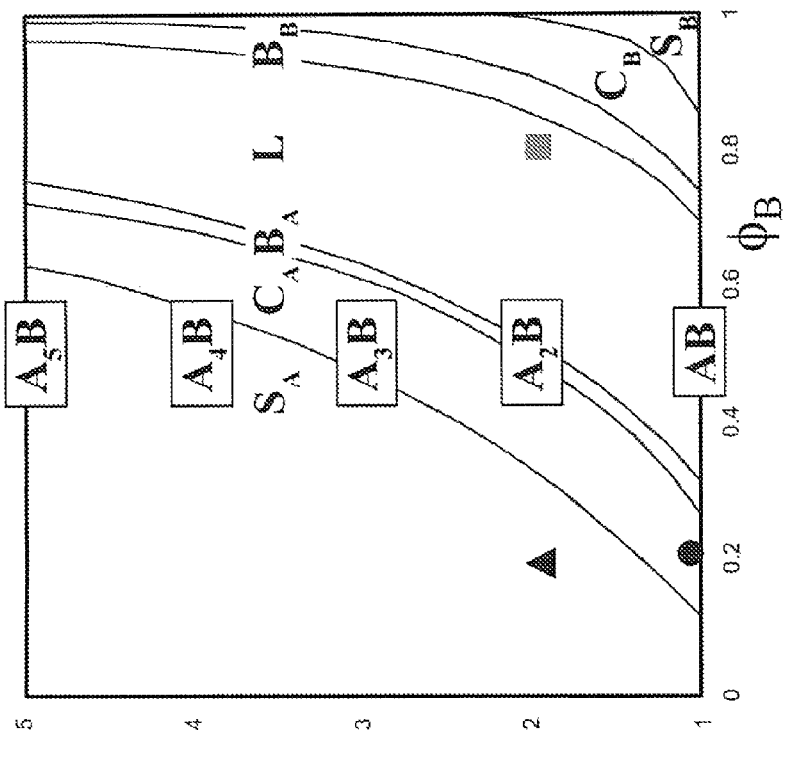
FIG. 4 are schematic drawings and a morphology diagram showing how Milner theory can be applied to regular multigraft copolymers by considering local asymmetry, imagining that the regular multigraft copolymers are strings of miktoarm stars. In the graph, epsilon ($\epsilon$) is a parameter that describes primarily the level of architectural asymmetry. Phi$_B$ ($\phi_B$) is the volume fraction of component B in the copolymer.
Figure 4:
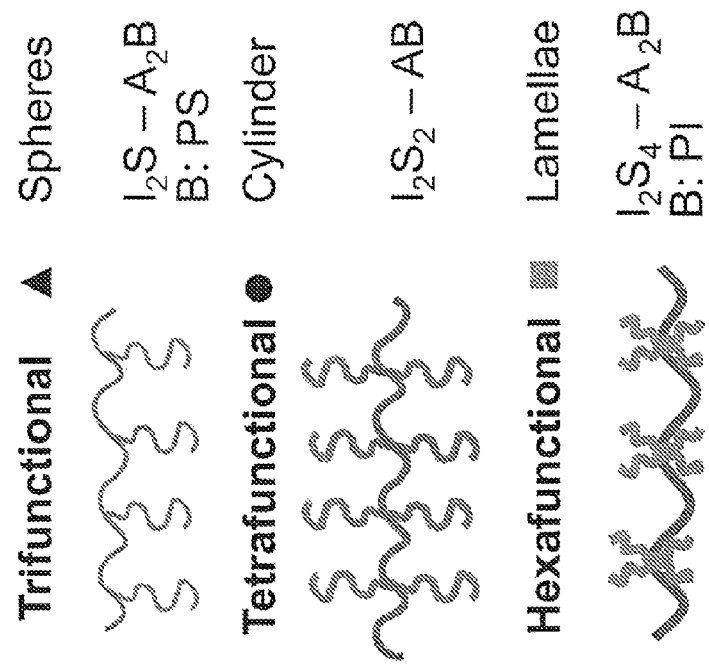

Previous characterization data on complex graft copolymer architectures with multiple grafting points has been fit into the framework of a theoretical morphology diagram (see FIG. 3) calculated by Milner, S. T., *Macromolecules*, 27, 2333 (1994), whose analysis predicts morphology as a function of composition and molecular asymmetry (architecture) for materials with a single junction point. For example, at $\epsilon=1$, the Milner diagram models linear, conformationally symmetric, AB diblock behavior with symmetric morphology windows around $\phi_B=0.5$. As the number of arms of one species increase relative to the other, however, the morphological behavior can become strongly asymmetric with respect to volume fraction. This behavior allows the sought after uncoupling of morphology from volume fraction to be achieved. Thus, the morphology can be varied independently of volume fraction by adjusting the molecular architecture. Milner's theory is not strictly applicable to more complex, multiple graft copolymer materials, however. The use of the building block principle of the constituting block copolymer to understand the morphological behavior of multiple graft materials by mapping them back to the more well-understood behavior of single graft materials has been required. As shown in FIG. 4, these ideas have been used to develop a rational framework for predicting the morphologies of all the types of molecular architecture shown in FIG. 1B.

Morphological characterization of regular tetrafunctional multiblock polymers is presented in FIGS. 2A-2D. Morphological characterization of these multigraft (or block) copolymers can utilize real-space, transmission electron microscope (TEM) imaging and reciprocal-space small angle scattering (SAXS and/or SANS) techniques.

Other things being equal (PS volume fraction and average number of grafts per molecule), in some embodiments of the presently disclosed subject matter, increasing junction point functionality increases material strength and elasticity. And for a fixed PS volume fraction and junction point functionality, in some embodiments of the presently disclosed subject matter, increasing the number of junction points per copolymer increases the strength, strain at break, and elasticity. In a representative comparison, the presently disclosed subject matter can compared to the strength, elasticity and strain at break performance of commercial thermoplastic elastomers, such as KRATON™ and STYROFLEX™ materials (Kraton Polymers, Houston, Tex., United States of America and BASF, Ludwigshafen, Germany, respectively).

Figure 5:
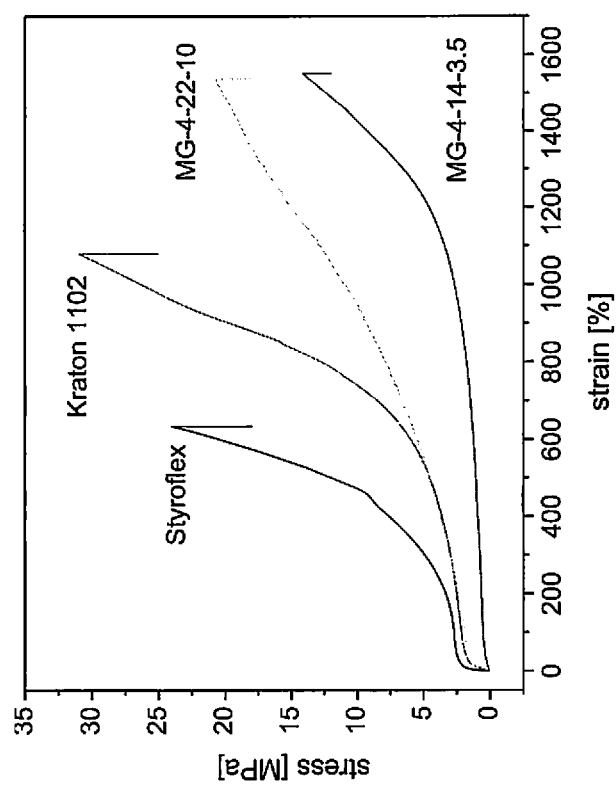
FIG. 5 is a graph showing the stress vs. strain tensile curves from data for STYROFLEX™, KRATON™, and two regular tetrafunctional graft polystyrene-polyisoprene copolymers. MG-4-22-10 has 22 volume % polystyrene (PS) and an average of 10 branch points. MG-4-14-3.5 has 14 volume % PS and an average of 3.5 branch points.

FIG. 5 provides a representative test that compares the stress versus strain curves for KRATON™ and STYROFLEX™ with previous data for two tetrafunctional multigraft copolymers comprising regularly spaced PS grafts and a polydiene backbone. Each of the multigraft copolymers comprises 22 volume % PS grafts. One (MG-4-22-10) has an average of 10 branch points, while the other (MG-4-14-3.5) has an average of 3.5 branch points. These tests utilize a scaled down ASTM standard "dog bone" and obtain good testing statistics by reusing broken tensile specimens to produce new specimens for further testing. This is done by re-dissolving the broken dog bones in solution, casting and annealing new sample films from which new dog bones are cut. In some embodiments, this representative test is employed with respect to the presently disclosed subject matter.

Figure 6A:
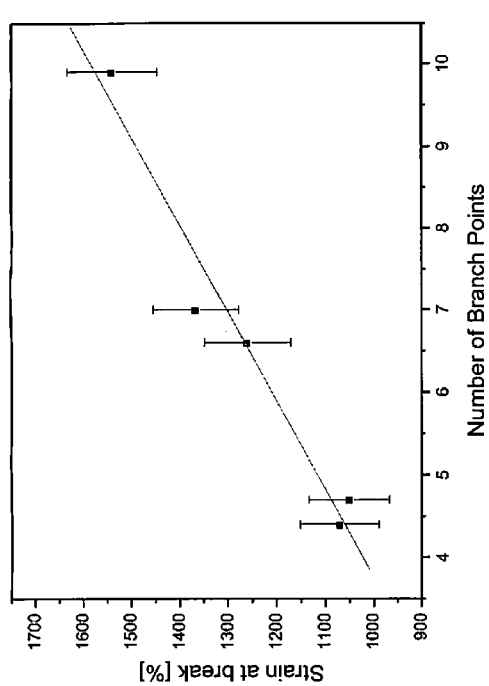
FIG. 6A is a graph of previous data showing the influence of the number of branch points of the % strain at break in regular multigraft copolymers. The average number of branch points in the copolymers varied from about 4.5 to about 10, while the chain lengths and PS volume % was held constant.
Figure 6B:
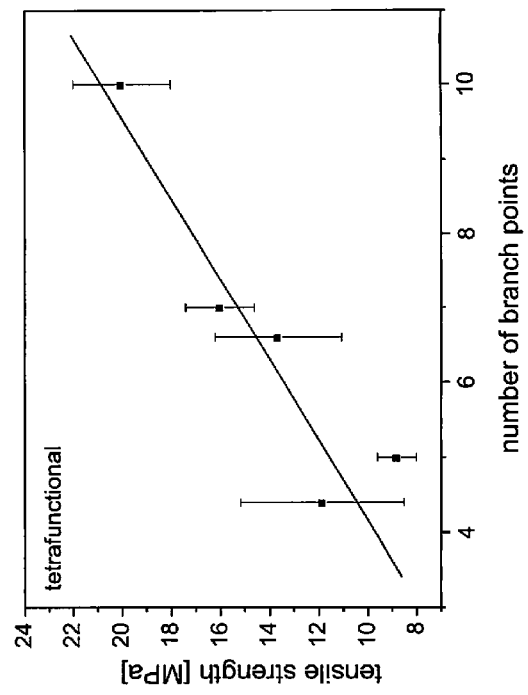
FIG. 6B is a graph of previous data showing the influence of the number of branch points on the tensile strength in regular tetrafunctional multigraft copolymers. The average number of branch points in the copolymers varied from a little over 4.0 to about 10, while the chain lengths and PS volume % was held constant.
Figure 6C:
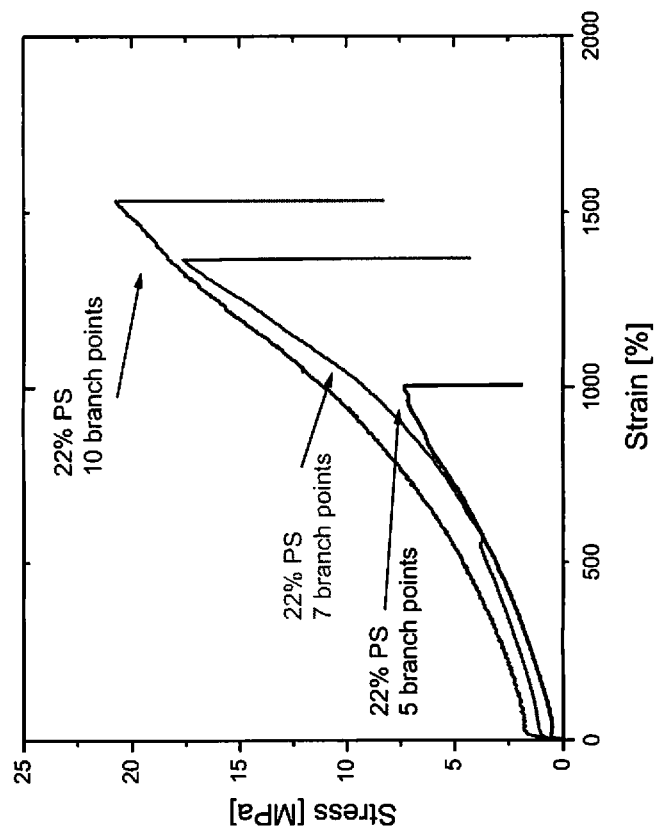
FIG. 6C is a graph of data showing the influence of the number of branch points on the stress versus strain curves for regular multigraft copolymers. The volume fraction of polystyrene was held at a constant 22% while the average number of branch points was 5, 7, or 10.
Figure 7:
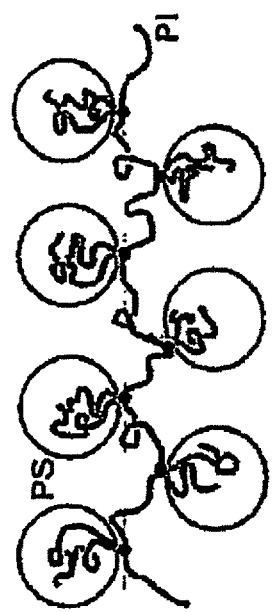
FIG. 7 is a schematic representation of microphase separation in a multigraft copolymer with tetrafunctional branch points. Reproduced from Weidisch et al., *Macromolecules*, 34, 6333 (2001).

FIGS. 6A-6C show representative tests that in some embodiments are applied to the presently disclosed subject matter. FIGS. 6A-6C show data indicating that both strain at break and tensile strength increase as the number of branch points is increased when segment lengths and composition is held constant. These data appear to reinforce the theory that multiple tethers lead to better load distribution. Without being bound to any one theory, it is believed that improved strain at break is due to enhanced load transfer between the rubbery backbone and the many dispersed glassy side chain domains. See FIG. 7. According to one aspect of the currently disclosed subject matter, randomly spaced side chains can take the place of the regularly spaced side chain glassy domains of FIG. 7, as it is believed that the number of side chains is of greater importance to the properties of the copolymer than the spacing of the side chains.

Figure 8A:
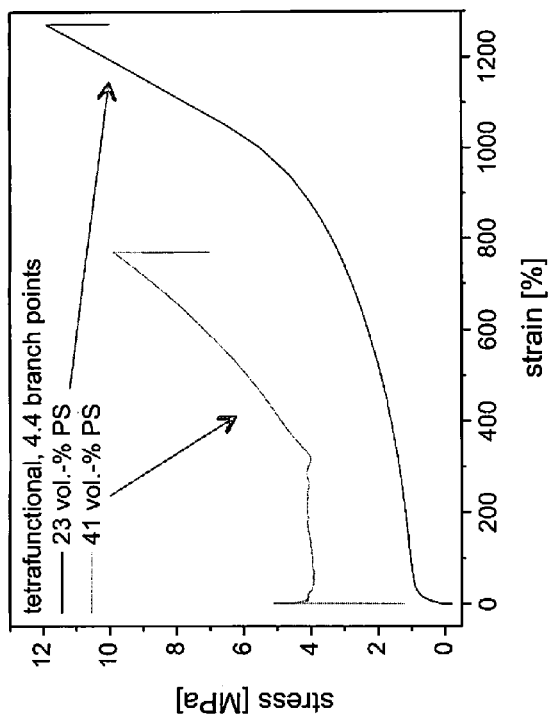
FIG. 8A is a graph of previous data showing the influence of chemical composition on the stress versus strain curves for two regular tetrafunctional multigraft copolymers. Both copolymers had an average of 4.4 branch points. One copolymer had 23 volume % polystyrene (PS) and the other had 41 volume % PS.
Figure 8B:
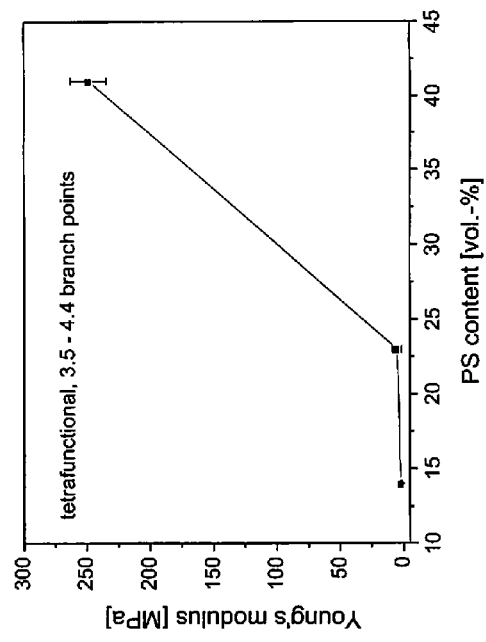
FIG. 8B is a graph of previous data showing the influence of chemical composition on Young's modulus for regular tetrafunctional multigraft copolymers having polystyrene volume % ranging from about 14% to about 40%. The copolymers had an average number of branch points between about 3.5 and about 4.4.

FIGS. 8A and 8B show representative tests that in some embodiments are applied to the presently disclosed subject matter. FIGS. 8A and 8B show previous data regarding the influence of glassy polymer content on the mechanical properties of regular multigraft copolymers. Increasing PS content increases stiffness of the copolymer.

Figure 9A:
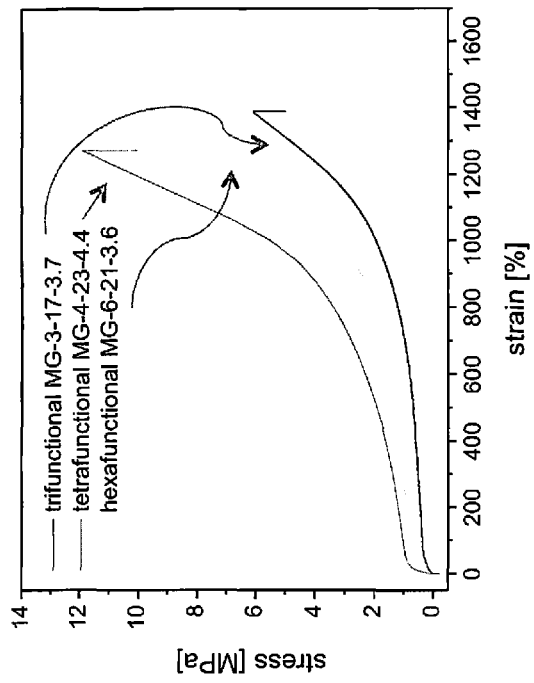
FIG. 9A is a graph of previous data showing the influence of branch point functionality on the stress versus strain curves of various regular multigraft copolymers. Trifunctional copolymer MG-3-17-3.7 has 17 volume % polystyrene and an average of 3.7 branch points. Tetrafunctional copolymer MG-4-23-4.4 has 23 volume % PS and an average of 4.4 branch points. Hexafunctional copolymer MG-6-21-3.6 has 21 volume % PS and an average of 3.6 branch points.
Figure 9B:
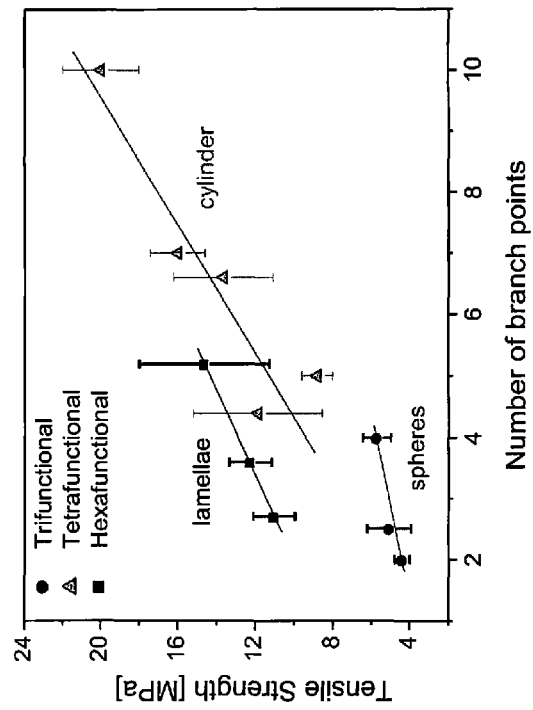
FIG. 9B is a graph of data showing the influence of morphology and number of branch points on tensile strength in regular multigraft copolymers having 20 volume % polystyrene (PS). Circles show the data for trifunctional copolymers, which had a spherical morphology. Triangles show data for tetrafunctional copolymers, which had a cylindrical morphology. Squares show data for hexafunctional copolymers, which had a lamellar morphology.

FIGS. 9A and 9B show representative tests that in some embodiments are applied to the presently disclosed subject matter. FIGS. 9A and 9B show the influence of branch point functionality on mechanical properties obtained from previous data with regular multigraft copolymers. As shown in FIG. 9B, at 20 vol % PS both the hexafunctional (lamellar) and tetrafunctional (cylinders) samples exhibit high tensile strength and elongations well over 1,000%, but show large differences in modulus. The trifunctional sample (spheres) is much softer and less strong but again has exceptional elongation at break. In short, the property profile can be tailored to meet a specific application by changing the architecture (branch point functionality) while keeping the chemical composition the same.

Figure 10:
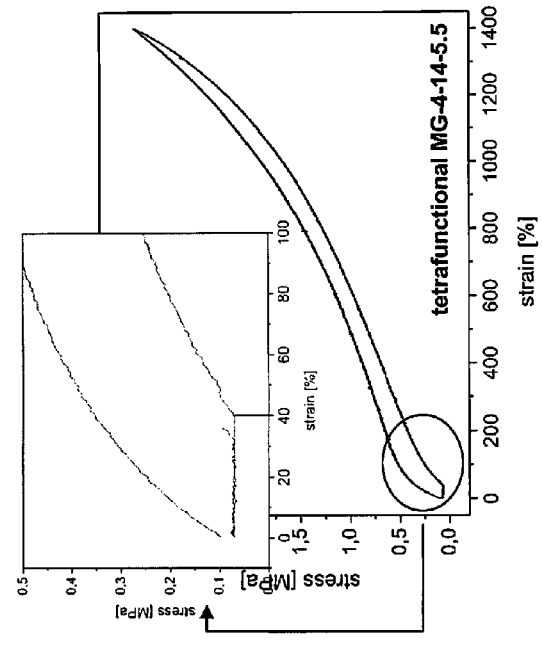
FIG. 10 is a series of graphs showing the hysteresis behavior of regular multigraft copolymers. The graphs show stress versus strain data for material that has been stretched and then the load is removed. The hypothetical sample that recovers its initial dimensions exactly has zero residual strain. The graph in the upper left-hand side is for a regular hexafunctional multigraft copolymer having 21 volume % polystyrene PS content and an average of 5.2 branch points. The graph in the upper right-hand side is for a regular tetrafunctional multigraft copolymer having 14 volume % PS content and an average of 5.5 branch points. The graph in the lower left for STYROFLEX™ is shown for comparison. As shown in the blown-up portion of the graph in the upper right, the residual strain for the tetrafunctional regular multigraft copolymer is only 40% at an applied strain of 1400%. Residual strains for STYROFLEX™ were larger.
Figure 10:
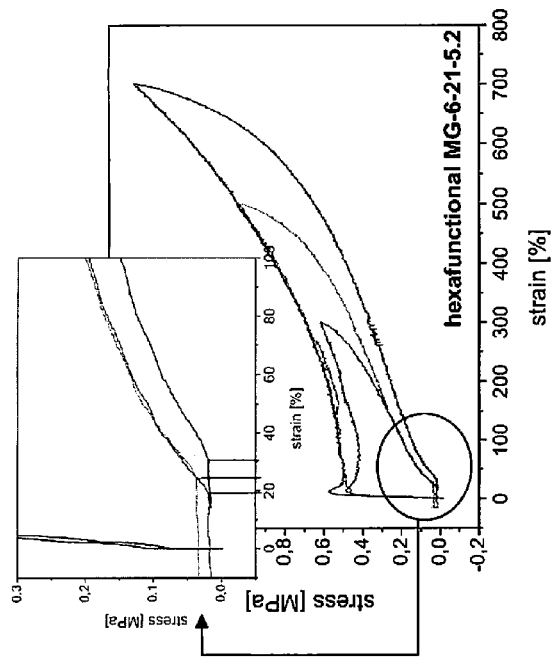
Figure 10:
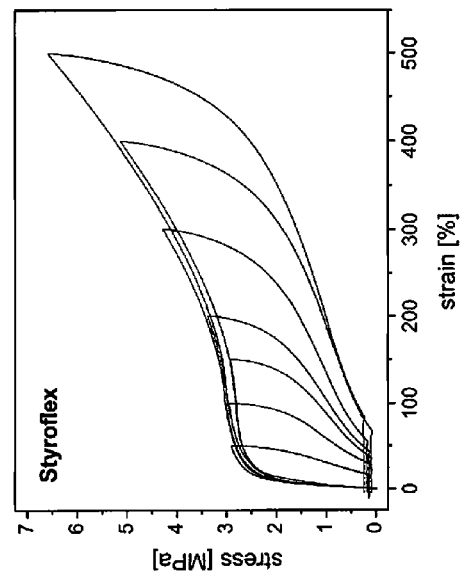
Figure 11:
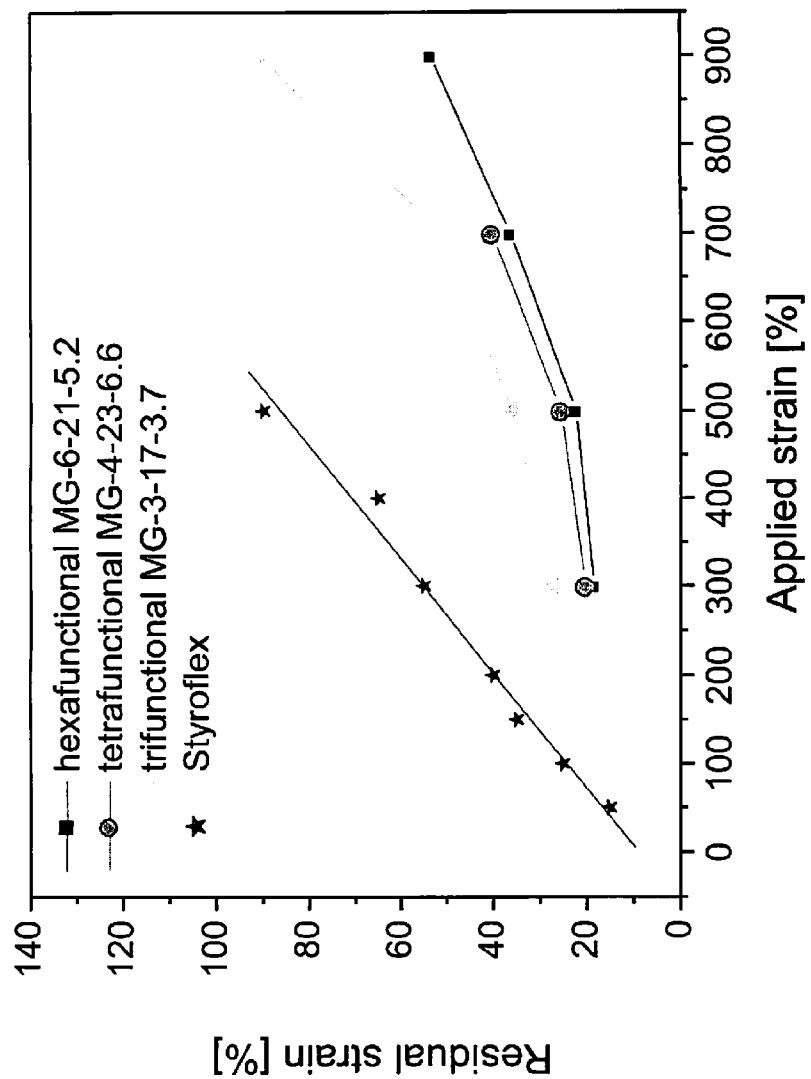
FIG. 11 is a graph of data showing the % residual strain versus the applied strain % for a hexafunctional regular multigraft copolymer having 21 volume % polystyrene (PS) and an average of 5.2 branch points (squares), a tetrafunctional regular multigraft copolymer having 23 volume % PS and an average of 6.6 branch points (circles), and a trifunctional regular multigraft copolymer having 17 volume % PS and an average of 3.7 branch points (triangles). Data for STYROFLEX™ (stars) is shown for comparison.

FIG. 10 shows representative tests that in some embodiments are applied to the presently disclosed subject matter. FIG. 10 shows previous stress versus strain data for regular multigrafts where the material has been stretched and then the load removed. Ideally the sample can recover its initial dimensions exactly (zero residual strain). The multigrafts (a hexafunctional sample on the left and a tetrafunctional sample on the right) show extraordinarily low residual strain, even when stretched far beyond what is possible with commercial linear TPEs. STYROFLEX™ data is shown for comparison at the bottom left side of FIG. 10. Residual strain for a multigraft tetrafunctional copolymer comprising 14 volume % PS grafts and an average of 5.5 branch points is only about 40% at an applied strain of 1400%. FIG. 11 shows representative tests that in some embodiments are applied to the presently disclosed subject matter. FIG. 11 shows additional previous data for PI-g-PS regular multigrafts summarized in a graph of residual strain versus applied strain. The elastic recovery is again believed to be due to having many sites along the backbone where the rubbery backbone is tethered to glassy domains.

If desired, in addition to tensile tests at room temperature, tensile performance at elevated temperatures can be evaluated, to determine material properties under conditions of any particular proposed use. Dynamical mechanical, creep, and fatigue performance of these materials at room and elevated temperatures can also be evaluated. Thermogravimetric analysis (TGA) can be used to investigate the chemical stability of the materials at elevated temperatures.

In some embodiments, the presently disclosed subject matter provides a composition comprising a random multigraft copolymer comprising a rubbery polymeric backbone and a plurality of glassy polymeric grafts, each attached at one of a plurality of randomly placed branch points on the polymeric backbone. The multigraft copolymer can comprise, for example a trifunctional comb architecture, in which a single graft is attached at each branch point, a tetrafunctional centipede architecture, in which two grafts are attached at each branch point, or a hexafunctional barbwire architecture, in which four grafts are attached at each branch point.

In some embodiments, "rubbery" refers to a polymer that has a glass transition temperature of about 0° C. or less (e.g., about 0, −10, −20, −30, −40, −50, −60, −70, −90, −100° C. or less). In some embodiments, the rubbery polymer backbone can comprise one of the polymers including, but not limited to, polyisoprene, hydrogenated polyisoprene, polybutadiene, hydrogenated polybutadiene, polyisobutylene, butyl rubber, poly(butadiene-co-acrylonitrile), a silicone rubber (e.g., polydimethylsiloxane or another siloxane polymer), acrylic rubber, polychloroprene, ethylene propylene copolymer, ethylene/acrylic elastomer, urethane rubber, and combinations thereof.

In some embodiments, "glassy" refers to a polymer that has a glass transition temperature of about 60° C. or more (e.g., about 60, 70, 80, 90, or 100° C. or more). As used herein "glassy" can include semi-crystalline polymers (e.g., having a melting point of about 60° C. or greater). In some embodiments, the glassy polymer grafts can comprise a polymer selected from, but not limited to, polystyrene, hydrogenated polystyrene, poly(α-methylstyrene) or another glassy styrenic polymer hydrogenated derivative thereof, polyethylene, urethane hard domain, polyester, polymethylmethacrylate or another glassy acrylic polymer, polyvinyl chloride, poly(vinyl pyridine), polycarbonate, nylon, polyethylene teraphthalate, polycyclohexadiene, hydrogenated polycyclohexadiene, and combinations thereof.

If desired, one or more of the copolymer components can include or be chemically functionalized to include an ionizable group (e.g., carboxylic acids, sulfonates, etc.). U.S. Pat. No. 7,619,036, for example, describes methods of sulfonating PS grafts in copolymers, thereby providing a material suitable for use as an ionomeric membrane, such as in fuel cells and other applications.

Typically, the volume fraction of the glassy polymeric grafts can be between about 5 and about 50%. In some embodiments, the volume fraction of glassy polymeric grafts is between about 14% and about 26% (e.g., about 14, 15, 16, 17, 18, 19, 20, 21, 22, 23, 24, 25, or 26%).

Generally, the random multigraft copolymer can comprise at least three branch points (i.e., an average of about 3 branch points). In some embodiments, the multigraft copolymer can comprise an average of at least four, five, six, seven, eight, nine, ten, twelve, fourteen or more branch points.

The copolymer can have any suitable molecular weight (i.e., any suitable average molecular weight). Typically, the molecular weights for the presently disclosed polymers are expressed as a number average molecular weight. In some embodiments, the copolymer can have a molecular weight of about 400,000 to about 600,000 (e.g., about 400,000, about 425,000, about 450,000, about 475,000, about 500,000, about 525,000, about 550,000, about 575,000, about 600,000). However, in some embodiments, the molecular weight can be smaller or greater. For example, in some embodiments, the molecular weight can be about 25,000 to about 400,000 (e.g., about 25,000, about 50,000, about 75,000, about 100,000, about 125,000, about 150,000, about 175,000, about 200,000, about 225,000, about 250,000, about 275,000, about 300,000, about 325,000, about 350,000, about 375,000, or about 400,000).

In some embodiments, e.g., using a macromonomer approach and anionic polymerization, the random multigraft copolymer can be synthesized to have a narrow molecular weight distribution (MWD). In some embodiments, the MWD is less than 2. In some embodiments, the MWD is less than about 1.5, 1.4, 1.3, 1.2, or less than 1.1. These narrow MWDs are in contrast to the MWDs of regular multigraft copolymers, which are typically at least about 2.

In some embodiments, the random multigraft copolymer can have a residual strain of about 55% or less (e.g., 55%, 50%, 45%, 40%, 35%, 30%, 25% or 20%) at an applied strain of about 500% or more (e.g., about 500%, 600%, 700%, 800%, 900%, 1000%, 1100%, 1200, 1300%, or 1400%). For example, the copolymer can have a residual strain of about 50% at an applied strain of 900%. In some embodiments, the copolymer can have a residual strain of about 40% or less at an applied strain of about 300% or more. In some embodiments, the copolymer can have a residual strain of about 40% at an applied strain of 1400%.

The presently disclosed copolymers typically have high strain at break. In some embodiments, the multigraft copolymer has a strain at break of about 1200% or greater (e.g., about 1200%, 1300%, 1400%, 1500%, etc.). In some embodiments, the random multigraft copolymer has a strain at break of at least 1500%. The percent strain at break can increase linearly with the number of branch points.

III. Compositions and Articles of Use Comprising Multigraft Copolymers

In view of the excellent mechanical properties of the presently disclosed materials, compositions comprising the materials can be provided for use in a wide variety of areas, both as high-tech and commodity thermoplastics. In particular, it is believed that the random multigraft copolymers disclosed herein can be prepared readily in large amounts and at relatively low cost, while still providing materials having high tensile strength, high elasticity, and high strain at break.

Accordingly, in some embodiments, the presently disclosed subject matter provides a thermoplastic elastomer composition comprising: a random multigraft copolymer comprising a rubbery polymeric backbone and a plurality of glassy or semi-crystalline polymeric grafts, wherein each of the plurality of glassy or semi-crystalline polymeric grafts is attached to the rubbery polymeric backbone at one of a plurality of randomly spaced branch points and at least one additional component, such as, but not limited to, an organic filler, an inorganic filler, a wax, a plasticizer, a tackifier, an anti-oxidant, a stabilizer (e.g., a thermal or UV stabilizer), a decorative agent, a biocide, a flame retardant, an anti-static agent, a therapeutic agent, a processing aid, such as a lubricant or a mold-release agent, and combinations thereof. The type and amount of an additive or additives can be chosen based on the properties desired for the final end use of the composition. The additive or additives can be present in an amount that is less than 50% by volume or by weight of the composition as a whole. Alternatively, the multigraft copolymer can comprise less than 50% of the composition as a whole.

The inorganic and organic fillers that can be used according to the presently disclosed subject matter can be of any known type and can have a form, such as but not limited to, granule, plate, lamella, fiber and whisker. The inorganic filler can be an inorganic-matter type filler, a metallic filler, a ceramics filler, etc. Examples of inorganic-matter type fillers include an oxide such as silica, diatomaceous earth, barium ferrite, berylium oxide, pumice and pumice balloon; a hydroxide such as aluminum hydroxide, magnesium hydroxide and basic magnesium carbonate; a carbonate such as calcium carbonate, magnesium carbonate, dolomite and dosonite; a sulfate or sulfite such as calcium sulfate, barium sulfate, ammonium sulfate and calcium sulfite; a silicate such as talc, clay, mica, asbestos, glass fiber, glass balloon, glass bead, calcium silicate, montmorillonite and bentonire; a carbon such as carbon black, graphite, carbon fiber and hollow carbon sphere; molybdenum sulfide; boron fiber; zinc borate; barium metaborate; calcium borate; and sodium borate. Examples of metallic fillers include metal elements, metal compounds, alloys, etc. each in the form of powder or granule, including a metal element or elements such as, but not limited to, zinc, copper, iron, lead, aluminum, nickel, chromium, titanium, manganese, tin, platinum, tungsten, gold, magnesium, cobalt and strontium; oxides thereof; alloys thereof, such as stainless steel, solder and brass. Metallic fibers can include, for example, aluminum fiber, stainless-steel fiber, copper fiber, bronze fiber, nickel fiber, potassium titanate fiber, other simple metal fibers and synthetic fibers and corresponding metal whiskers. Examples of the ceramics fillers include silicon carbide, silicon nitride, zirconia, aluminum nitride, titanium carbide each in the form of powder, granule, fiber or whisker. Thus, inorganic fillers include, but are not limited to, Inorganic fillers, can include, but are not limited to, carbonates (e.g., calcium carbonate), oxides of varying hydration levels (e.g., titanium dioxide), sulfates (e.g., barium sulfate), silicates (e.g., calcium or magnesium silicates), talc, amorphous silica, silica gel, carbon black, and clays (e.g., kaolin).

Examples of organic fillers include, but are not limited to shell fiber such as husk, wooden powder, cotton, jute, paper pieces, cellophane pieces, aromatic polyamide fiber, polyimide fiber, cellulose fiber, nylon fiber, polyester fiber, polypropylene fiber and thermosetting resin powders.

Waxes suitable for use in the presently disclosed compositions include, but are not limited to, paraffin waxes, microcrystalline waxes, polyethylene waxes, polypropylene waxes, by-product polyethylene waxes, Fischer-Tropsch waxes, oxidized Fischer-Tropsch waxes and functionalized waxes such as hydroxy stearamide waxes and fatty amide waxes. It is common in the art to use the terminology synthetic high melting point waxes to include high density low molecular weight polyethylene waxes, by-product polyethylene waxes and Fischer-Tropsch waxes. Modified waxes, including vinyl acetate modified waxes such as AC-400 (Honeywell International Inc., Morristown, N.J., United States of America) and MC-400 (available from Marcus Oil and Chemical Company, Houston, Tex., United States of America), maleic anhydride modified waxes such as Epolene C-18 (available from Eastman Chemical, Kingsport, Tenn., United States of America) and AC-575A and AC-575P (available from Honeywell International Inc., Morristown, N.J., United States of America) and oxidized waxes can be used in the presently disclosed compositions. Typically, if used, the wax can be present in an amount of between about 2% and about 25%.

Plasticizers for use in the presently disclosed compositions can include any plasticizer known in the art, including, but not limited to, ester plasticizers, such as phthalates, trimellitates, adipates, sebacates, and maleates; benzoates; epoxidized vegetable oil, paraffin or a chlorinated paraffin, sulfonamides, polyethers, glycols, organophosphates, and alkyl citrates. Plasticizers can also include, for example, paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available.

Suitable tackifiers include any compatible resins or mixtures thereof such as: (1) natural or modified rosins such, for example, as gum rosin, wood rosin, tall-oil rosin, distilled rosin, hydrogenated rosin, dimerized rosin, and polymerized rosin; (2) glycerol and pentaerythritol esters of natural or modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) natural terpenes and copolymers and terpolymers of natural terpenes, e.g., styrene/terpene and alpha methyl styrene/terpene; (4) polyterpene resins and hydrogenated polyterpene resins; (5) phenolic modified terpene resins and hydrogenated derivatives thereof, for example, as the resin product resulting from the condensation, in an acidic medium, of a bicyclic terpene and phenol; (6) aliphatic petroleum hydrocarbon resins, e.g., resulting from the polymerization of monomers consisting of primarily of olefins and diolefins; and hydrogenated aliphatic petroleum hydrocarbon resins; (7) alicyclic petroleum hydrocarbon resins and the hydrogenated derivatives thereof; and (8) aliphatic/aromatic or cycloaliphatic/aromatic copolymers and their hydrogenated derivatives. Specific polyterpene tackifiers include, for example, WINGTACK® 95 from Goodyear (Goodyear Tire and Rubber Company, Akron, Ohio, United States of America). Specific cycloaliphatic resins include, for example, EASTOTAC™ H100R from Eastman Chemical (Kingsport, Tenn., United States of America). In some embodiments, the tackifier is selected from the group comprising rosins and derivatives thereof, terpenes, modified terpenes, an aliphatic resin, a cycloaliphatic resin, an aromatic resin, a hydrogenated hydrocarbon resin, a terpene-phenol resin, and mixtures thereof.

Anti-oxidant additives and stabilizers (e.g., thermal or UV stabilizers) can be used to protect the copolymers and copolymer compositions from degradation during the fabrication and/or use of the articles comprising the compositions. Thus, for example, UV stabilizers can protect the articles from degradation due to exposure to light. Antioxidants typically used in the production of pressure sensitive adhesives can be present in an amount of up to about 3 wt %. Stabilizers can include, but are not limited to, epoxides, sterically hindered phenols, butylated hydroxytoluene (BHT), benozophenones, amines (e.g., hindered aromatic amines), thioesters, phosphites, and triazine-, piperidine-, and benzotriazoles. Sterically hindered phenols utilized herein include, for example, high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. Representative hindered phenols include: 1,3,5-trimethyl 2,4,6-tris(3,5-di-tert-butyl-4-hydroxybenzyl)benzene; pentaerythrityl tetrakis-3(3,5-di-tert-butyl-4-hydroxyphenyl)-propionate; 4,4'-methylenebis(2,6-tert-butylphenol); 4,4'-thiobis(6-tert-butyl-o-cresol); 2,6-di-tert-butylphenol; 6-(4-hydroxyphenoxy)-2,4-bis(n-octylthio)-1,2,5-triazine; di-n-octadecyl-3,5-di-tert-butyl-4-hydroxybenzyl phosphonate; 2-(n-octylthio)ethyl 3,5-di-tert-butyl-4-hydroxybenzoate; and sorbitol hexa[3-(3,5-di-tert-butyl-4-hydroxyphenyl)-propionate].

Decorative agents include materials added to enhance the visual appeal of the article prepared from the presently disclosed composition. Thus, decorative agents include, but are not limited to, pigments, dyes or other colorants, and materials such as glitter or metallic dust. For example, the composition can contain metallic pigments (aluminum and brass flakes), $TiO_2$, mica, fluorescent dyes and pigments, phosphorescent pigments, aluminatrihydrate, antimony oxide, iron oxides iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. In some embodiments, other additives can be added to increase other aspects of the aesthetic appeal of the articles prepared from the presently disclosed compositions, such as, for example a fragrance.

The presently disclosed compositions can obtained by mixing and homogenizing the components by the usual methods of plastics technology, and the sequence of adding the components may be varied. Examples of suitable mixing equipment are continuous or batch kneaders, compounding rolls, plastographs, Banbury mixers, co-rotating or counter rotating single- or twin-screw extruders, or other mixers which will provide essentially homogeneous mixtures. In some embodiments, the presently disclosed compositions are prepared by blending together the components including the multigraft copolymer and other additive or additives as desired at between about 23° C. to about 100° C., forming a paste like mixture, and further heating said mixture uniformly (e.g., to about 150° C., or to about 200° C. or more) until a homogeneous molten blend is obtained. Any heated vessel equipped with a stirrer can be used, including those equipped with components to pressure and/or vacuum.

The thermoplastic properties of the presently disclosed copolymers and compositions lend themselves to the fabrication of a variety of articles, via molding and other methods of fabrication known in the art, including, but not limited to injection molding, compression molding, extrusion, and calendering. Accordingly, in some embodiments, the presently disclosed subject matter provides a fabricated article comprising a random multigraft copolymer. The fabricated articles can be for example an automotive interior or exterior part (e.g., an air bag or air bag door, a seat covering (such as artificial leather upholstery), bumpers, decorative molding pieces, etc.); shoe soles or other shoe parts; elastic waistbands; diaper or sanitary napkin backings or attachments; adhesive tapes, membranes, toys (or parts for toys), balloons, bags, tubing, roofing tiles, medical devices, and electronic wiring coatings or other electronic device components. For example, U.S. Patent Application Publication No. 2009/0028356 describes the use of elastomeric polymers as an expandable bubble portion in an audio device. In some embodiments, the compositions can be used to provide elastic or flexible moldings for "soft-touch" applications, such as grips, handles, antislip surfaces, gaskets, switches, housings with sealing lips, control knobs, flexographic printing plates, hoses, profiles, medical items, hygiene items, such as toothbrushes, materials for insulating or sheathing cables, sound-deadening elements, folding bellows, rolls or roll coatings, and carpet backings.

In some embodiments, the article is a medical device. Medical devices can include, but are not limited to, infusion kits, dialysis units, breathing masks, catheter tubing, intravenous (iv) bags or tubing therefore, blood bags, syringes, prosthetics, implants or implant coverings (e.g., orthopedic implants, stents or other endoprostheses, or coverings for pacemakers or cochlear implants). In some embodiments, the article is a balloon catheter or a stent. For example, the article can comprise a balloon catheter wherein at least the inflatable portion of the balloon catheter comprises the presently disclosed thermoplastic elastomer composition.

Catheters can include any tubing (e.g., flexible or "soft" tubing) that can be inserted into a body cavity, duct, or vessel to inject or to drain fluids. The body cavity, duct, or vessel can be for example, the urethra, the bladder, a blood vessel (e.g., a vein or artery), a biliary duct, the kidney, the heart, the uterus, a fallopian tube, the epidural space, the subarchnoid space, etc. Balloon catheters include an inflatable balloon at or near the tip of the catheter (i.e., the "distal" end, the end of the catheter to be inserted into the body). The catheter is inserted into the body vessel or cavity with the balloon deflated. Upon insertion into a vessel or cavity in the body, the balloon can be inflated to remove a blockage or otherwise expand a narrow passageway in the body. The balloon can then be deflated again for removal of the catheter. The balloon catheter can be inserted into the body to deliver a stent. For example, the stent can be placed over the balloon portion of the catheter for insertion into the body. When placed inside the body at the desired location (e.g., in a blocked artery), the balloon can be inflated, thereby expanding the stent. The balloon can then be deflated and the catheter removed, leaving the stent in position within the body.

Stents are tubular, radially expandable (e.g., self-expandable or balloon expandable) articles for insertion into a narrow passage in the body to increase flow through the passage. Thus, for example, the stent can be used to treat or prevent a disease-induced narrowing of a body cavity, such as, for example, to increase blood flow through an artery damaged by atherosclerosis. Various stents are described, for example, in U.S. Pat. No. 4,886,062, incorporated herein by reference in its entirety.

Stents can have one or more branch points. For example, stents can be y-shaped, including a central main tube portion that at one end is separated into two tubes. Stents can be fabricated from metal, polymers, or combinations thereof. For example, the stent can include a wire mesh, a metal coil or coils, or metal rings covered by and/or connected with the presently disclosed composition. Alternatively, the stent can comprise the presently disclosed composition alone or as a covering for another polymeric material.

Figure 12A:
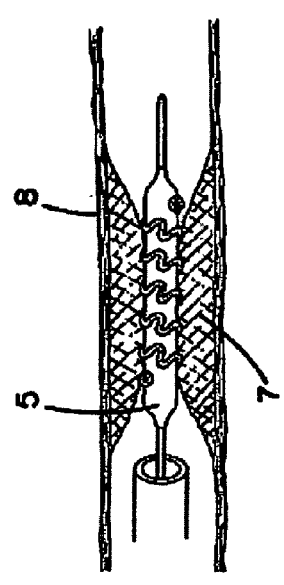
FIG. 12A is a schematic drawing showing a balloon catheter assembly inside a partially occluded vessel per U.S. Pat. No. 4,886,062.
Figure 12B:
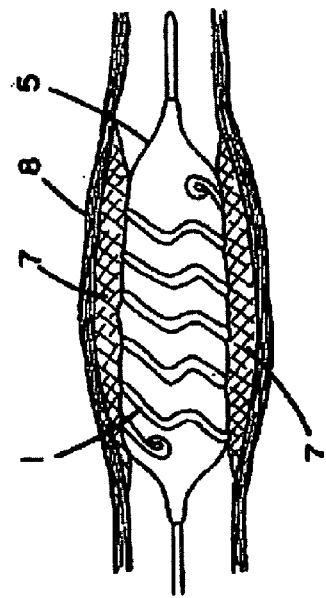
FIG. 12B is a schematic drawing showing a balloon catheter assembly with a stent inside a partially occluded vessel per U.S. Pat. No. 4,886,062 with the balloon inflated and the stent radially expanded.
Figure 12C:
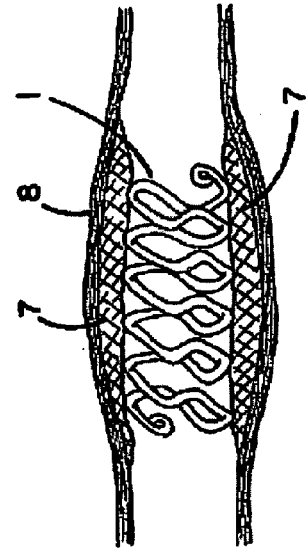
FIG. 12C is a schematic drawing showing a stent inside a vessel per U.S. Pat. No. 4,886,062.
Figure 14:
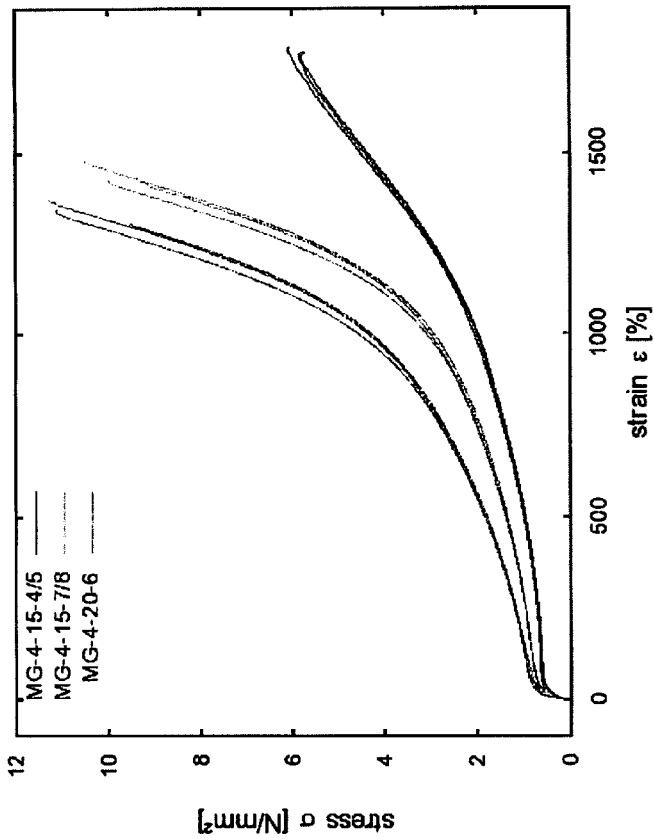
FIG. 14 is a graph of data showing tensile characteristics of random multigraft copolymers including strain at break, tensile strength and elastic modulus.
Figure 15:
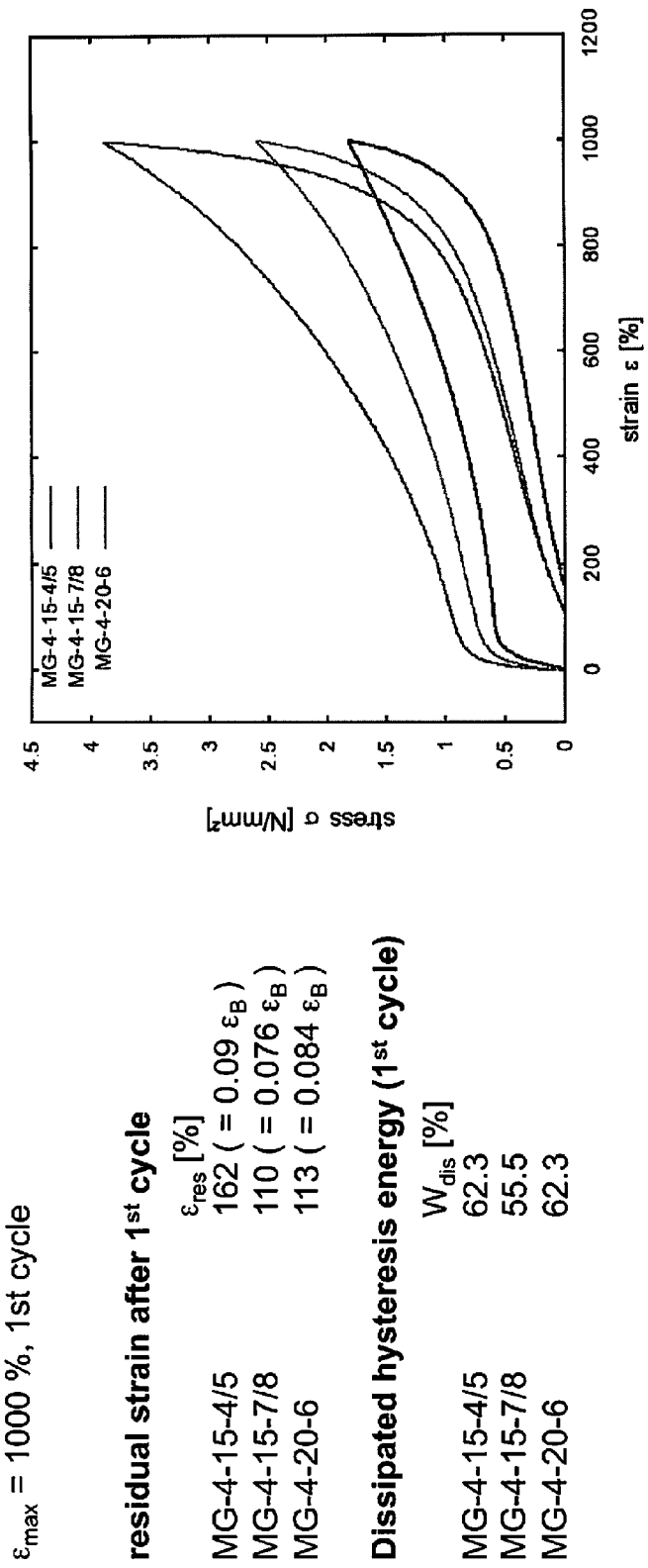
FIG. 15 is a graph of data showing hysteresis of random multigraft copolymers including residual strain after the first cycle and dissipation hysteresis energy after the first cycle at $\epsilon_{max}=1000\%$.
Figure 16:
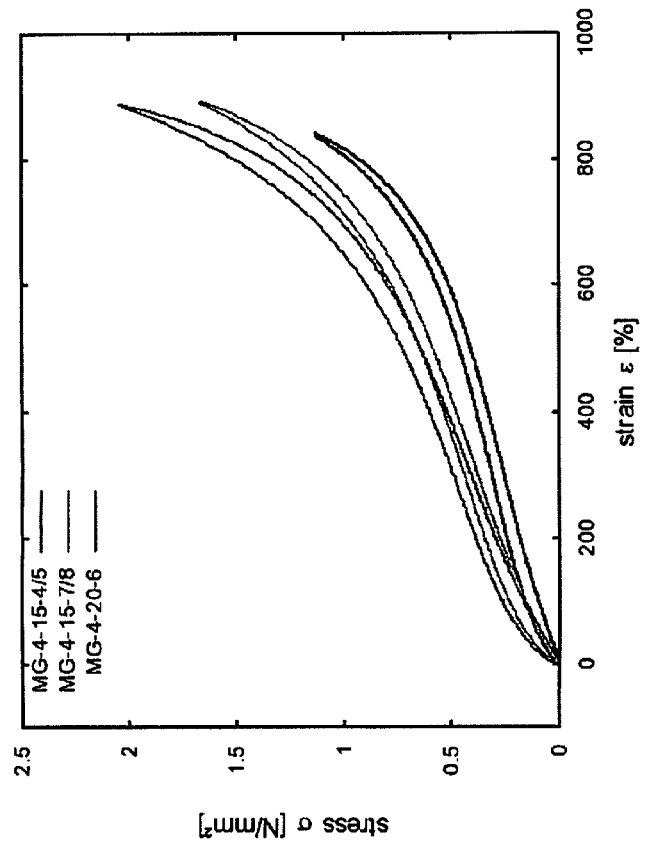
FIG. 16 is a graph of data showing hysteresis of random multigraft copolymers including residual strain after the second cycle and dissipation hysteresis energy after the second cycle at $\epsilon_{max}=1000\%$.
Figure 17:
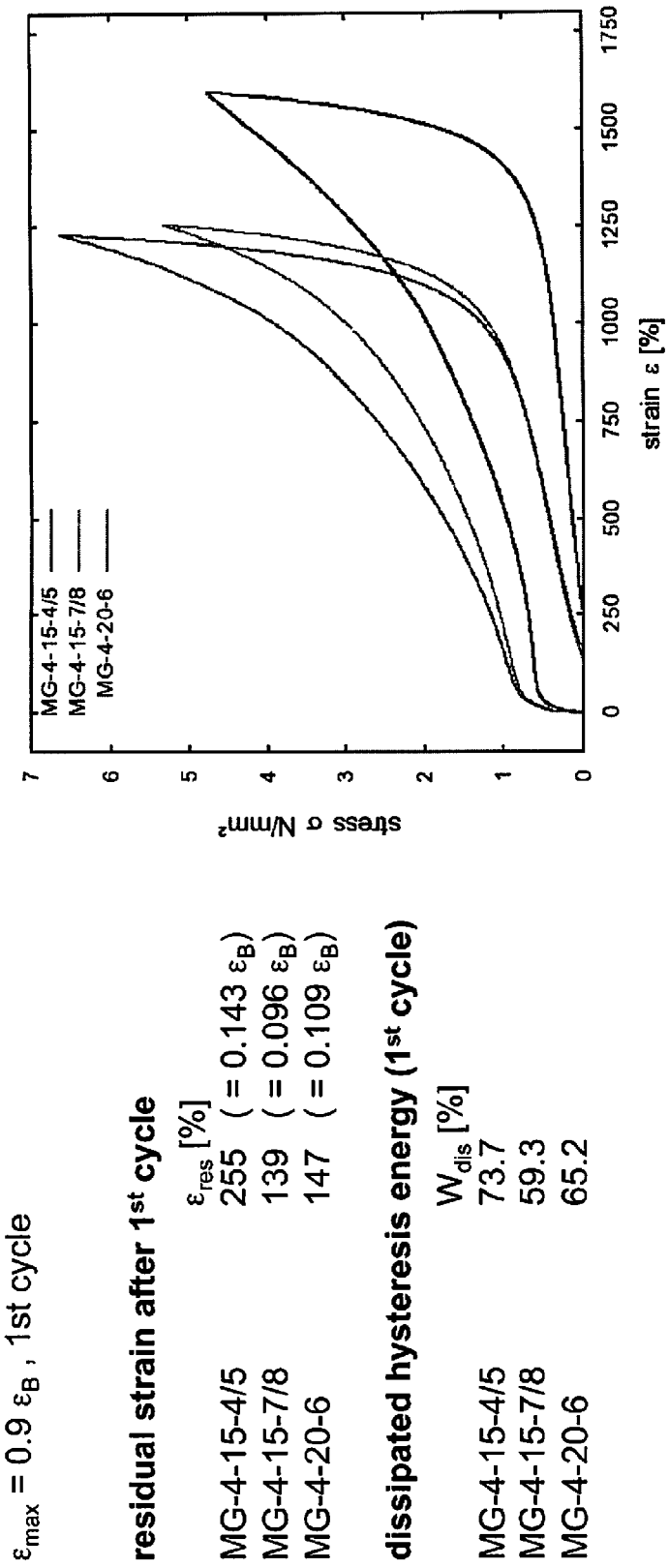
FIG. 17 is a graph of data showing hysteresis of random multigraft copolymers including residual strain after the first cycle and dissipation hysteresis energy after the first cycle at $\epsilon_{max}=0.9\ \epsilon_B$.
Figure 18:
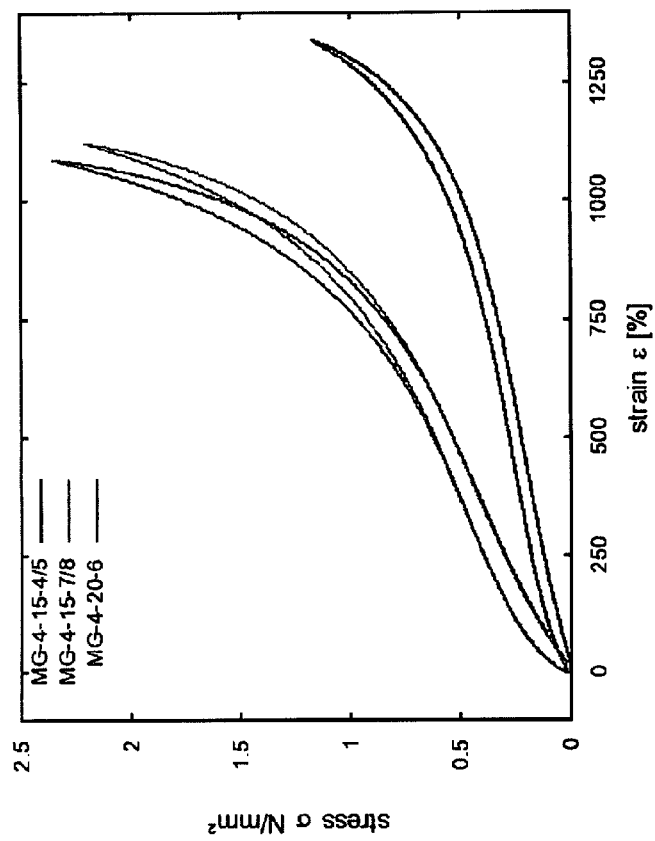
FIG. 18 is a graph of data showing hysteresis of random multigraft copolymers including residual strain after the second cycle and dissipation hysteresis energy after the second cycle at $\epsilon_{max}=0.9\ \epsilon_B$.

FIGS. 12A-12C, reproduced from U.S. Pat. No. 4,886,062 show how a balloon catheter assembly can be used to place a metallic coil stent into a vessel. In FIG. 12A, balloon catheter 5 is shown positioned against blockage 7 in vessel 8. The blockage can be a plaque in a blood vessel. The balloon catheter extends from a guiding catheter shown at the left-hand side of the drawing. In FIG. 12B, the balloon of balloon catheter 5 is inflated, thereby radially expanding stent 1, compressing blockage 7. In FIG. 12C, the balloon catheter has been removed, leaving behind expanded stent 1, holding blockage 7 open in vessel 8.

U.S. Pat. No. 7,794,491, incorporated herein by reference in its entirety, also shows an exemplary method of how a balloon catheter can be used to deploy a stent. FIGS. 13A-13D are reproduced from U.S. Pat. No. 7,794,491. As shown in FIG. 13A, balloon catheter 32, is positioned in vessel V, so that deflated balloon 30, of balloon catheter 32, is parallel to target site T. Stent I surrounds deflated balloon 30. In FIG. 13B, balloon 30 is inflated, radially expanding stent I so that stent I contacts the sides of vessel V at target site T. In FIG. 13C, balloon 30 of balloon catheter 32 is deflated so that the balloon no longer contacts the inner circumference of stent I. Stent I remains in position in contact with the sides of vessel V at site T. In FIG. 13D, balloon catheter 32 has been removed from vessel V, leaving stent I at site T. FIG. 13D shows polymer coating C covering stent I, thereby forming a continuous surface connecting an underling metal or metallic component (e.g., a wire coil or coils or a wire mesh).

The stent can be coated with a drug-eluting coating or the thermoplastic elastomeric composition can include a therapeutic additive, which can elute from the composition upon placement in the body or upon exposure to particular conditions (e.g., heat, pH, enzymes, etc.). For example, the multigraft copolymer can be blended with a biodegradable polymer having an encapsulated or otherwise complexed drug.

U.S. Pat. No. 5,837,008; U.S. Pat. No. 5,851,217; U.S. Pat. No. 5,873,904 and U.S. Pat. No. 6,344,035 describe the incorporation of drugs in multiple layers of a single polymer on stents, wherein the drug-polymer layers are applied in one or more consecutive applications. Thus, for example, in the presently disclosed subject matter, a multigraft copolymer stent or multigraft copolymer covered stent can be further covered with a drug layer. The drug layers can be covered with a bioabsorbable polymer, such as poly (L-lactic acid), poly(lactide-co-glycolide), or poly(hydroxybutyrate-co-valerate).

U.S. Pat. No. 5,843,172 describes a porous metallic stent in which a drug is loaded into the pores of the metal. The stent can also have a polymeric cover, which can contain a different drug than the drug loaded into the metal pores. The drug can also be provided in the form of drug-eluting polymeric components located along the inner wall of the stent. U.S. Pat. Nos. 7,163,555, and 7,435,255, incorporated herein by reference in their entirety, describe drug eluting stents and stent frameworks comprising a plurality of drug eluting reservoirs.

The drug in the drug-eluting coating or the therapeutic agent added as an additive to the thermoplastic elastomer composition can be a therapeutic that prevents thrombus formation or restenosis. In some embodiments, the drug or therapeutic agent is selected from the group consisting of a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, a retinoid, a flavonoid, a carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator, such as those described hereinbelow.

In some embodiments, the presently disclosed compositions are provided for use as adhesive materials. Thus, in some embodiments, the presently disclosed subject matter provides an adhesive comprising:

a random multigraft copolymer comprising a rubbery polymeric backbone and a plurality of glassy or semi-crystalline polymeric grafts, wherein each of the plurality of glassy or semi-crystalline polymeric grafts is attached to the rubbery polymeric backbone at one of a plurality of randomly spaced branch points; and a tackifier. The adhesive can be a pressure sensitive adhesive or a hot melt adhesive and can be used, for example, to adhere plastics to other plastics or to other materials (e.g., paper, wood, metal, glass, etc.).

The tackifier can be any suitable tackifier as described hereinabove. The adhesive can further comprise one or more other additives, such as, but not limited to, waxes, plasticizers, anti-oxidants, UV-stabilizers, decorative agents, biocides, flame retardants, anti-static agents, and fillers. The adhesive can be formulated to provide either temporary or permanent adhesion.

The presently disclosed adhesive compositions can be used, for example, to act as a releasable adhesive for holding gift cards or other plastic cards onto paper or other backings for temporary display or presentation purposes. Thus, the adhesive can be present as a strip mounted between and in contact with a gift card and a gift card holder. When the gift card is pulled away from the holder, the adhesive releases from the gift card or the holder. The strip of adhesive can then be pulled off either the gift card or the holder, if desired, manually.

The presently disclosed adhesive compositions can also be provided in the form of adhesive tapes, comprising one or more releasable backing components that can be easily removed just prior to use of the adhesive. The compositions can further be provided as adhesive backings on other materials, e.g., labels, stamps, automotive trim, bandages or other wound care items, drug patches, diapers, etc. In some embodiments, the adhesive compositions can be provided in the form of spheres, bars or rods suitable for use as hot-melt adhesives, in the home, e.g., for various arts or crafts projects, or in industry, e.g., for the construction of cardboard boxes or for the fabrication of sporting equipment or toys.

The presently disclosed compositions are also useful as elastic or flexible coating layers over other objects, particularly for "soft-touch" applications. "Soft touch" applications include those, for instance, for which one or more of a soft texture, shock absorption, ergonomic comfort, slip resistance, and flexibility, are desirable.

Thus, in some embodiments, the presently disclosed subject matter provides a coated object comprising a coating layer comprising a random graft copolymer, wherein the random multigraft copolymer comprises a rubbery polymeric backbone and a plurality of glassy or semi-crystalline polymeric grafts, wherein each of the plurality of glassy or semi-crystalline polymeric grafts is attached to the rubbery polymeric backbone at one of a plurality of randomly spaced branch points, wherein the coating layer covers at least a portion of a surface of a wood, ceramic, glass, carbon fiber, metal, metallic, leather, fabric, stone, or plastic object. In some embodiments, the object is selected from the group comprising an article of clothing (e.g., a shoe or a portion of a shoe, such as a shoe sole, for orthopedic, athletic, or children's shoes or for work boots), an eating or cooking utensil (e.g., baby spoons or other infant feeding tools where a soft mouth feel might be needed, knives, tongs, vegetable peelers, etc), tools (e.g., hammers, wrenches, screwdrivers, saws, etc.), medical implants (e.g., stents, pacemakers, cochlear implants), medical/surgical tools (e.g., retractors, scalpels, clamps, etc.) and wiring and electronic devices (e.g., electronic wiring or fiber optic wiring, materials in ear buds).

In some embodiments, the coated object comprises a stent, wherein the stent comprises metal or metallic wire mesh or coil(s) having a cylindrical shape, covered by the coating layer. Suitable metals and metallic materials for forming the stent framework, such as the mesh or coil(s), include, but are not limited to, stainless steel, platinum, titanium, tantalum, nickel-titanium, cobalt, chromium, and alloys thereof.

In some embodiments, wherein the thermoplastic elastomeric composition is being used as a drug-releasing coating, such as for a medical implant or other medical device, such as stent, the composition can include a therapeutic agent, such as but not limited to, a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, a retinoid, a flavonoid, a carotenoid, a lipid improving agent, a DNA synthesis inhibitor, a tyrosine kinase inhibitor, an antiplatelet, a vascular smooth muscle antiproliferative agent, an antiinflammatory agent, a biological material, an interferon, and a NO production accelerator. Carcinostatics can include, but are not limited to, vincristine sulfate, vinblastine sulfate, vindesine sulfate, irinotecan hydrochloride, paclitaxel, docetaxel hydrate, methotrexate and cyclophosphamid. Immunosuppressives can include, but are not limited to, sirolimus, tacrolimus hydrate, azathioprine, cyclosporin, mycophenolatemofetil, gusperimus hydrochloride, and mizoribine. Antibiotics include, but are not limited to, mitomycin C, doxorubicin hydrochloride, actinomycin D, daunorubicin hydrochloride, idarubicin hydrochloride, pirarubicin hydrochloride, aclarubicin hydrochloride, epirubicin hydrochloride, peplomycin sulfate, and zinostatin stimalamer.

Antirheumatics can include, but are not limited to, sodium aurothiomalate, penicillamine, and lobenzarit disodium. Aantithrombotics can include, but are not limited to, heparin, ticlopidine hydrochloride, and hirudin. Antihyperlipidemics can include HMG-CoA reductase inhibitors and probucol. HMG-CoA reductase inhibitors can include, but are not limited to, serivastatin sodium, atolvastatin, nisvastatin, pitavastatin, fluvastatin sodium, simvastatin, lovastatin, and pravastatin potassium. ACE inhibitors include, but are not limited to, quinapril hydrochloride, perindopril erbumine, trandolapril, cilazapril, temocapril hydrochloride, delapril hydrochloride, enalapril maleate, lisinopril, and captopril.

Calcium antagonists can include, but are not limited to, nifedipine, nilvadipine, diltiazem hydrochloride, benidipine hydrochloride, and nisoldipine. Antiallergics include, but are not limited to, tranilast. Retinoids can include, but are not limited to, all-trans retinoic acid.

Antioxidants include catechines (e.g., epigallocatechin gallate), anthocyanine, proanthocyanidin, lycopene, and β-carotene. Tyrosine kinase inhibitors include, but are not limited to, genistein, tyrphostin, and apstatin.

Antiinflammatories include, but are not limited to, dexamethasone, prednisolone, and other steroids, and aspirin. The therapeutic agent can also include a therapeutic biological material, such as, but not limited to, EGF (epidermal growth factor), VEGF (vascular endothelial growth factor), HGF (hepatocyte growth factor), PDGF (platelet derived growth factor), and BFGF (basic fibroblast growth factor).

Medical implants and medical/surgical tools coated with or comprising the presently disclosed compositions can be provided for use in both human medical applications and in veterinary applications. Thus, in some embodiments, the presently disclosed subject matter provides an object for implantation (e.g., a stent) in a subject, either permanently or temporarily. The subject is desirably a human subject, although it is to be understood that all vertebrate species are intended to be included in the term "subject." The presently disclosed subject matter described herein provides articles particularly useful in the treatment and/or prevention of diseases or during surgical intervention in warm-blooded vertebrates. Thus, the presently disclosed articles can be used for the treatment of mammals and birds.

More particularly, provided herein are articles for the treatment of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, llamas, giraffes, deer, goats, bison, and camels), and horses. Also provided herein are articles for the treatment of birds, including the treatment of those kinds of birds that are endangered, kept in zoos or as pets (e.g., parrots), as well as fowl, and more particularly domesticated fowl, i.e., poultry, such as turkeys, chickens, ducks, geese, guinea fowl, and the like, as they also are of economical importance to humans. Thus, embodiments of the articles described herein can be used in the treatment of livestock, including, but not limited to, domesticated swine (pigs and hogs), ruminants, horses, poultry, and the like.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Synthesis of Random Multigraft Copolymers

The synthesis of random multigraft copolymers comprising, for example, PS side chains and a PI backbone, can be based on the use of macromonomers bearing one or more PS side chains, prepared by anionic polymerization or other polymerization methods, followed by the living anionic copolymerization of the macromonomer with isoprene to create the graft copolymer. See, e.g., Driva et al., *J. Polym.*

*Sci.: Polym. Chem.*, 43, 4470-4078 (2005); and Rahman et al., *Macromolecules*, 41, 8225-8230 (2008). In contrast to previous studies, where branch point spacing was carefully controlled (see Uhrig and Mays, *Macromolecules*, 35, 7182-7190 (2002)), the random placement of the grafts can be achieved by the use of a potassium alkoxide as an additive during the anionic copolymerization of the styrene-based macromonomer and the isoprene. See Driva et al., *J. Polym. Sci.: Polym. Chem.*, 43, 4470-4078 (2005). Polymers can be prepared having 15 weight % PS side chains. For trifunctional comb polymers, the branch molecular weight can be about 32,000 and for the tetrafunctional centipede polymers the branch molecular weight can be 16,000. The total molecular weight can be about 400,000 or about 600,000. The multigraft copolymers can be characterized, for example, by SEC with light scattering detection, differential refractometry, and NMR. Morphology of pressed polymer sheets can be performed via SAXS and synchrotron SAXS. Additional studies including mechanical testing, modeling, hysteresis and softening characterization can be performed by methods known in the art. See, e.g., Schlegel, et al., *Polymer*, 50, 6297-6304 (2009); Thunga et al., *KGK*, 9, 597-605 (2008); Staudinger et al., *Eur. Polym. J.*, 44, 3790-3796 (2008); Duan et al., *Macromolecules*, 42, 4155-4164 (2009).

Example 2

General Methods for Morphological Characterization

The following procedure is a representative method by which the morphology of a block or graft copolymer is evaluated. This procedure is the same general approach that has been employed in previous block copolymer research on PS-polydiene materials to produce a sample representative of the equilibrium morphology, and to evaluate that morphology. See Gido, S. P., et al., *Macromolecules*, 29, 7022 (1996); Gido, S. P., et al., *Macromolecules*, 30, 6771 (1997); Pochan, D. J., et al., *Macromolecules*, 29, 5091 (1996); Pochan, D. J., et al., *J. Polymer Sci.: Part B, Polymer Physics*, 35, 2629 (1997); Lee, C., et al., *J. Chem. Phys.*, 107, 6460 (1997); Lee, C., et al., *Macromolecules*, 30, 3732 (1997); Lee, C., et al., *Polymer*, 19, 4631 (1998); Xenidou, M., et al., *Macromolecules*, 31, 7659 (1998); Beyer, F. L., et al., *Macromolecules*, 30, 2373 (1997); Bever, F. L., et al., *Macromolecules*, 32, 6604 (1999); Beyer, F. L., et al., *J. Polymer Sci.: Part B, Polymer Physics*, 37, 3392 (1999); Bever, F. L., et al., *Macromolecules*, 33, 2039 (2000); Burgaz, E., et al., *Macromolecules*, 33, 8739-8745 (2000); Alward, D. B., et al., *Macromolecules*, 19, 215 (1986); Thomas, B. L., et al., *Macromolecules*, 20, 2934 (1987); Thomas, B. L., *Macromolecules*, 19, 2197 (1986); Gido, S. P. et al., *Macromolecules*, 26, 4506 (1993); and Winev, K. I., et al., *J. Chem. Phys.*, 95, 9367 (1991).

Solid films of the block or graft copolymer material, approximately 1- to 3-mm thick, are cast from solution. Toluene is the standard non-preferential solvent for polystyrene (PS) and polyisoprene (PI). Casting from other solvents that are selective for either PS or PI can result in shifts in morphology away from that which the molecule itself would prefer. The degree of long-range order in the samples can then be increased by thermal annealing at about 120° C. These casting and annealing conditions have been found to promote self-assembly of well-ordered, nanostructured morphologies in previous studies of graft copolymers.

After annealing, ultrathin sections approximately 30-80 nm thick are prepared for TEM observation by cryoultramicrotoming. The sections of PS-PBD materials are stained in $OsO_4$ vapors for about four hours to react with the PBD block double bonds, rendering these blocks dark in TEM imaging via mass thickness contrast. See Kato, K., *Polymer Engineering and Science*, 8, 38 (1967); and Kato, K., *J. Polymer Sci., B* 4, 35 (1966).

Small angle scattering experiments can be performed on all samples to accurately determine the lattice symmetries and spacings of the morphologies. Small angle X-ray scattering (SAXS) and small angle neutron scattering (SANS) can be used to study model graft copolymers. SAXS can be performed, for example, by using a rotating anode source and a two-dimensional area detector.

Example 3

Synthesis and Molecular Characterization of Random Multigraft Copolymers

The synthesis of the multigraft copolymers having double polystyrene side chains or grafts randomly placed on a polyisoprene backbone (random tetrafunctional multigrafts) followed generally the published procedure of Driva et al. (P. Driva, H. Iatrou, D. J. Lohse, and N. Hadjichristidis, J. Polym. Sci., Part A, Polym. Chem., 43, 4070 (2005)). These workers reported the synthesis of comb branched polybutadienes having both a polybutadiene backbone and double polybutadiene grafts. However, in the present example the double tailed macromonomers were based on polystyrene side chains and the backbone was polyisoprene.

The purification and synthesis of reagents were carried out using vacuum line conditions as described by Uhrig and Mays (D. Uhrig and J. Mays, J. Polym. Sci., Part A, Polym. Chem., 43, 6179 (2005)). 4-(Dichloromethylsilyl)styrene (DCMSS) was prepared using the Grignard reaction of 4-chlorostyrene with trichloromethylsilane. Each polymer synthesis was based from about 240 µmol DCMSS (480 µmol Si—Cl), which was titrated with poly(styryllithium) (PSLi) of the desired molecular weight, previously endcapped with 3-4 units of butadiene, to the 2-equiv point, which was 480 µmol anion, monitored by aliquots and the use of gel permeation chromatography monitoring, on the order of 5 g PSLi for each one depending on the molecular weight ($M_W$) and everything diluted at this point with about 300-400 ml benzene in the reactor. Then, on the order of 20 g isoprene was added, along with fresh sec-BuLi (approximately 30-50 µmol depending on the experiment), and potassium 2,3-dimethyl-pentoxide-3 (ROK), approximately 1-2 µmol (⅟₃₀ of the sec-BuLi), and more benzene for final a volume of 700 ml. The reaction was allowed to proceed several days to one week before terminating by addition of degassed methanol, and in some instances a trace of unincorporated macromonomer remained. The weight-average molecular weights ($M_W$) and polydispersity indices (PDIs) for the multigrafts were determined by GPC with light scattering detection. PDIs of the multigrafts were in the range of about 1.1-1.2.

Other molecular characteristics of the three samples were as follows.

MG-4-15-7/8:
PS arm $M_W$=8.0 kg/mol; Multigraft $M_W$=807 kg/mol; 15% PS

MG-4-15-4/5:
PS arm $M_W$=8.0 kg/mol; Multigraft $M_W$=434 kg/mol; 15% PS

MG-4-20-6:
PS arm $M_w$=10.0 kg/mol; Multigraft $M_w$=566 kg/mol; 20% PS

The foregoing three random multigraft copolymers were each cast from solutions with toluene (approximately 4 wt. %). The solvent was slowly evaporated over 7 days and the cast polymer films were annealed at 70° C. under vacuum for 3 days to remove residual toluene.

Dog bone shaped specimen (according to DIN EN ISO 527/type 5B) were stamped from the films, which obtain a thickness of about 0.4-0.7 mm.

Tensile and hysteresis tests were carried out on a Zwick/Roell universal testing machine equipped with a 100 N load cell. The strain was measured using an extensometer (Zwick/Roell MultiXtens). This strain sensor shows extremely low contract force and enables strain measurements at deformations larger than 1000%. The contact points of the extensometer and the clamping device were covered by tape to prevent the sample from damage and slippage. The three random multigraft copolymers were deformed by a cross head speed of 33 mm/min resulting in a strain rate of 0.023 s$^{-1}$.

The results of the testing on the three random multigraft copolymers are shown in FIGS. 14-18.

Tensile Behavior

With increasing number of branch points, the tensile strength is decreasing, whereas the strain at break ($\epsilon_B$) and the Young's modulus are increasing (compare MG-4-15-4/5 and MG-4-15-7/8). Increasing styrene content leads to a higher tensile strength ($\sigma_B$) and a higher Young's modulus (compare MG-4-20-6 with the random multigrafts, containing 15 wt. % Styrene).

Hysteresis Test at $\epsilon_{max}$=1000%

MG-4-15-7/8 obtains the lowest residual strain ($\epsilon_{res}$) in the hysteresis test after deformation up to $\epsilon_{max}$. The dissipation hysteresis in the first cycle is quite large (62% for MG-4-15-4/5 and MG-4-20-6). In the second cycle, this parameter is decreasing to about 10-12% for all investigated materials.

Hysteresis Test at $\epsilon_{max}$=0.9 $\epsilon_B$

Similar values for $\epsilon_{res}$ were expected if the samples are deformed to a maximum strain with respect to their strain at break $\epsilon_B$. The results of MG-4-15-7/8 and MG-4-20-6 may support this assumption. MG-4-15-7/8 reveals also the lowest $\epsilon_{res}$ and the lowest dissipated hysteresis energy under these test conditions. However, the hysteresis tests of MG-4-20-6 at $\epsilon_{max}$=0.9 $\epsilon_B$ shows a significantly larger $\epsilon_{res}$ compared to the hysteresis tests at $\epsilon_{max}$=1000%.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A thermoplastic elastomer composition comprising:
    a random multigraft copolymer comprising:
        a rubbery polymeric backbone comprising a plurality of randomly spaced branch points, wherein the rubbery polymeric backbone comprises polyisoprene, hydrogenated polyisoprene, polybutadiene, hydrogenated polybutadiene, polyisobutylene, acrylic rubber, or combinations thereof; and
        a plurality of glassy or semi-crystalline polymeric grafts comprising polystyrene, poly(a-methylstyrene) or another glassy styrenic polymer, polymethylmethacrylate or another glassy acrylic polymer, or combinations thereof, and
    wherein each of the plurality of glassy or semi-crystalline polymeric grafts is attached to the rubbery polymeric backbone at one of the plurality of randomly spaced branch points; and wherein the random multigraft copolymer has a weight average molecular weight of about 400,000 or more, a volume fraction of glassy or semi-crystalline polymeric graft between about 14% and about 26%, and a strain at break of 1300% or greater.

2. The composition of claim 1, further comprising at least one additional component selected from an organic filler, an inorganic filler, a wax, a tackifier, a plasticizer, an antioxidant, a stabilizer, a decorative agent, a biocide, a flame retardant, an anti-static agent, a therapeutic agent or combinations thereof.

3. The composition of claim 2, wherein the decorative agent is a pigment or a dye.

4. The composition of claim 1, wherein the random multigraft copolymer has a residual strain of about 55% or less at an applied strain of about 500% or more.

5. The composition of claim 1, wherein the random multigraft copolymer has a residual strain of about 40% or less at an applied strain of about 300% or more.

6. The composition of claim 1, wherein the random multigraft copolymer has a strain at break of at least 1500%.

7. The composition of claim 1, wherein the random multigraft copolymer has a percent strain at break that increases linearly with the number of branch points.

8. The composition of claim 1, wherein the random multigraft copolymer comprises an architecture selected from a trifunctional comb architecture, a tetrafunctional centipede architecture, or a hexafunctional barbwire architecture.

9. The composition of claim 1, wherein the random multigraft copolymer comprises at least three branch points.

10. The composition of claim 1, wherein the random multigraft copolymer has a weight average molecular weight of between about 400,000 and about 600,000.

11. A fabricated article comprising the thermoplastic elastomer composition of claim 1.

12. The fabricated article of claim 11, wherein the article is prepared by injection molding, compression molding, extrusion, or calendering.

13. The article of claim 11, wherein the article comprises automotive interior or exterior parts, shoe soles or other shoe parts, elastic waistbands, diaper backings or attachments, adhesive tapes, membranes, balloons, bags, ribbing, roofing tiles, medical devices, electronic wiring coatings, or electronic device components.

14. The article of claim 13, wherein the article is a medical device selected from a balloon catheter or a stent.

15. The article of claim 14, wherein the article is a balloon catheter, and wherein at least the inflatable portion of the balloon catheter comprises the thermoplastic elastomer composition.

16. An adhesive comprising:
    a random multigraft copolymer comprising:
        a rubbery polymeric backbone comprising a plurality of randomly spaced branch points, wherein the rubbery polymeric backbone comprises polyisoprene, hydrogenated polyisoprene, polybutadiene, hydrogenated polybutadiene, polyisobutylene, acylic rubber, or combinations thereof; and
        a plurality of glassy or semi-crystalline polymeric grafts comprising polystyrene, poly(a-methylstyrene) or another glassy styrenic polymer, polymethylmethacrylate or another glassy acrylic polymer, or combinations thereof, and wherein each of the plurality of glassy or semi-crystalline polymeric grafts is attached to the rubbery polymeric backbone at one of the plurality of randomly spaced branch points; and wherein the random multigraft copolymer has a weight average molecular weight of about 400,000 or more, a volume fraction of glassy polymeric graft between about 14% and about 26%, and a strain at break of 1300% or greater; and a tackifier.

17. The adhesive of claim 16, wherein the random multigraft copolymer comprises an architecture selected from a trifunctional comb architecture, a tetrafunctional centipede architecture, or a hexafunctional barbwire architecture.

18. The adhesive of claim 16, wherein the adhesive is a pressure sensitive adhesive or a hot melt adhesive.

19. The adhesive of claim 16, wherein the tackifier comprises rosins and derivatives thereof, terpenes, modified terpenes, an aliphatic resin, a cycloaliphatic resin, an aromatic resin, a hydrogenated hydrocarbon resin, a terpene-phenol resin, or mixtures thereof.

20. The adhesive of claim 16, further comprising one or more additives selected from waxes, plasticizers, anti-oxidants, stabilizers, decorative agents, biocides, flame retardants, anti-static agents, or fillers.

21. The adhesive of claim 20, wherein the decorative agent is a pigment, a dye or glitter.

22. A coated object comprising a coating layer wherein the coating layer comprises the random multigraft copolymer of claim 1, wherein the coating layer covers at least a portion of a surface of a wood, ceramic, glass, carbon fiber, metal, metallic, leather, fabric, stone, or plastic object.

23. The coated object of claim 22, wherein the object comprises an article of clothing, an eating/cooking utensil, a medical implant, a medical/surgical tool, or an electronic device.

24. The coated object of claim 22, wherein the object comprises a medical implant or a medical/surgical tool and wherein the coating layer further comprises a therapeutic agent additive selected from the group consisting of a carcinostatic, an immunosuppressive, an antibiotic, an antirheumatic, an antithrombotic, an antihyperlipidemic, an ACE inhibitor, a calcium antagonist, an integrin inhibitor, an antiallergic, an antioxidant, a GPIIb/IIIa antagonist, a retinoid, a flavonoid, a carotenoid, a lipid improving agent, a DNA synthesis inhibitor, a tyrosine kinase inhibitor, an antiplatelet, a vascular smooth muscle antiproliferative agent, an antiinflammatory agent, an interferon, and a NO production accelerator.

25. The coated object of claim 22, wherein the coated object comprises a stent, wherein the stent comprises a metal or metallic wire mesh or a metal or metallic coil having a cylindrical shape, wherein the wire mesh or coil is covered by the coating layer.

26. A thermoplastic elastomer composition comprising:
a random multigraft copolymer comprising:
a rubbery polymeric backbone comprising a plurality of randomly spaced branch points; and
a plurality of glassy or semi-crystalline polymeric grafts, wherein each of the plurality of glassy or semi-crystalline polymeric grafts is attached to the rubbery polymeric backbone at one of the plurality of randomly spaced branch points;
and wherein the random multigraft copolymer has a weight average molecular weight of about 400,000 or more, a volume fraction of glassy polymeric graft between about 14% and about 26%, and a strain at break of 1300% or greater.

27. The thermoplastic elastomer composition of claim 26, wherein the random multigraft copolymer is prepared by copolymerization of macromonomers comprising a glassy or semi-crystalline polymer and monomers of the polymer of the rubbery polymeric backbone.

28. The thermoplastic elastomer composition of claim 26, wherein the rubbery polymeric backbone has a glass transition temperature of about −40° C. or less.

29. The thermoplastic elastomer composition of claim 26, comprising an average of three, four, five, six, seven, eight, or nine branch points.

* * * * *